US009709492B2

(12) United States Patent
Phillips et al.

(10) Patent No.: US 9,709,492 B2
(45) Date of Patent: Jul. 18, 2017

(54) TURBIDITY SENSING FILTER APPARATUS, SYSTEMS, AND METHODS THEREOF

(71) Applicants: FLSMIDTH A/S, Valby (DK); Mike Phillips, Bethlehem, PA (US)

(72) Inventors: Mike Phillips, Bethlehem, PA (US); Flemming Jørgensen, Copenhagen (DK); Robert Singer, Bethlehem, PA (US); Anders Fougner, Værløse (DK); Alexander Helm, Allerød (DK)

(73) Assignee: FLSMIDTH A/S, Valby (DK)

( * ) Notice: Subject to any disclaimer, the term of this patent is extended or adjusted under 35 U.S.C. 154(b) by 0 days.

(21) Appl. No.: 14/427,342

(22) PCT Filed: Oct. 15, 2013

(86) PCT No.: PCT/US2013/065034
§ 371 (c)(1),
(2) Date: Mar. 11, 2015

(87) PCT Pub. No.: WO2014/062670
PCT Pub. Date: Apr. 24, 2014

(65) Prior Publication Data
US 2015/0316474 A1 Nov. 5, 2015

Related U.S. Application Data

(60) Provisional application No. 61/714,036, filed on Oct. 15, 2012.

(51) Int. Cl.
*C02F 1/00* (2006.01)
*B01D 35/00* (2006.01)
(Continued)

(52) U.S. Cl.
CPC ............ *G01N 21/53* (2013.01); *B01D 25/004* (2013.01); *B01D 25/12* (2013.01); *B01D 25/215* (2013.01);
(Continued)

(58) Field of Classification Search
None
See application file for complete search history.

(56) References Cited

U.S. PATENT DOCUMENTS 2,562,181 A   7/1951   Frommer
3,319,514 A   5/1967   McAllister
(Continued)

FOREIGN PATENT DOCUMENTS

GB   2264882 A     9/1993
WO   9623208 A1   8/1996
(Continued)

OTHER PUBLICATIONS

The International Search Report and Written Opinion dated Mar. 4, 2014, 10 pages.
(Continued)

*Primary Examiner* — Richard Gurtowski
(74) *Attorney, Agent, or Firm* — Jeffrey A. Sharp

(57) ABSTRACT

A filter press having a plurality of stackable filter plate assemblies comprises at least one turbidity sensing module [20, 220, 320, 420] coupled to a first filter plate assembly [1] within the plurality of stackable filter plate assemblies. The turbidity sensing module [20, 220, 320, 420] is generally positioned between a filtrate drain opening [8a-d] communicating with a filter chamber [14], and either a filtrate port [7, 13] or filtrate discharge tube [4g, 15], in order to determine a level of turbidity of filtrate [50] exiting said first filter plate assembly. Turbidity levels may be determined independently of turbidity levels of filtrate [50] exiting other
(Continued)

filter plate assemblies [1] within the filter press. When turbidity levels reach a predetermined threshold, and alarm [80] is activated, which informs an operator of the need to replace a filter cloth associated with the affected filter plate assembly [1].

20 Claims, 12 Drawing Sheets

(51) Int. Cl.
    *B01J 49/00*      (2017.01)
    *G01N 21/53*      (2006.01)
    *B01D 25/12*      (2006.01)
    *B01D 25/00*      (2006.01)
    *B01D 25/21*      (2006.01)
    *B01D 29/00*      (2006.01)
    *B01D 65/00*      (2006.01)
    *G01N 21/47*      (2006.01)

(52) U.S. Cl.
    CPC ....... *G01N 21/532* (2013.01); *B01D 29/0018* (2013.01); *B01D 65/00* (2013.01); *G01N 2021/4711* (2013.01); *G01N 2201/062* (2013.01)

(56) References Cited

U.S. PATENT DOCUMENTS

| | | | |
|---|---|---|---|
| 3,669,267 A | | 6/1972 | Hutton |
| 3,974,068 A | * | 8/1976 | Ebner ................... B01D 35/00 210/321.84 |
| 4,198,298 A | | 4/1980 | Zuckerman et al. |
| 4,492,868 A | | 1/1985 | Jelvestam et al. |
| 5,445,745 A | * | 8/1995 | Handtmann ........... B01D 25/26 210/143 |
| 7,875,169 B2 | | 1/2011 | Klessling et al. |
| 2003/0035105 A1 | * | 2/2003 | Quist ..................... G01N 15/14 356/338 |
| 2010/0097605 A1 | * | 4/2010 | Murakami ............. B01D 61/20 356/337 |
| 2010/0170854 A1 | | 7/2010 | Casbeer et al. |
| 2011/0043807 A1 | | 2/2011 | Andelic et al. |
| 2011/0046787 A1 | * | 2/2011 | Booth ................... B01D 61/12 700/271 |
| 2011/0271518 A1 | | 11/2011 | Metzger |

FOREIGN PATENT DOCUMENTS

| | | |
|---|---|---|
| WO | 02068941 A1 | 9/2002 |
| WO | 2012060778 A1 | 5/2012 |

OTHER PUBLICATIONS

The European Search Report and Search Opinion dated May 17, 2016, 7 pages.

\* cited by examiner

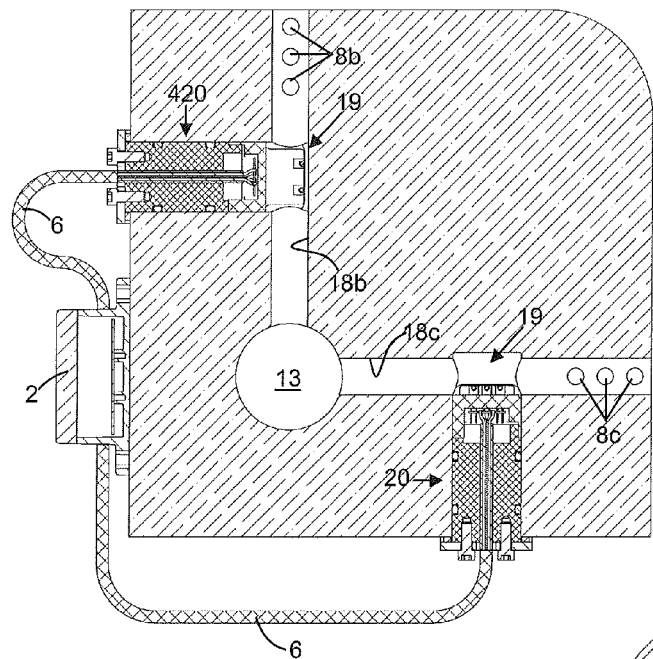
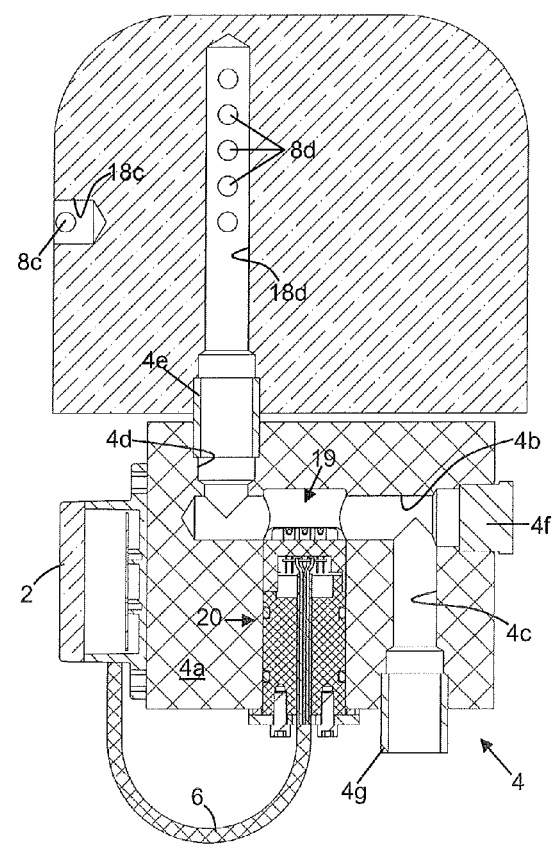
FIG. 5
FIG. 6

|  | Remote | Local |
|---|---|---|
| No Fault | "1" | Alarm OFF |
| New Fault | "0" | Alarm ON |
| Rectified Fault | "0" | Alarm ON |
| Rectified Fault and Reset | "1" | Alarm OFF |

TURBIDITY SENSING FILTER APPARATUS, SYSTEMS, AND METHODS THEREOF

CROSS-REFERENCE TO RELATED APPLICATIONS

This PCT application claims the benefit of U.S. provisional application No. 61/714,036 filed on 15 Oct. 2012.

FIELD OF THE INVENTION

This invention relates to filtration equipment used in the industrial, waste, tailings, coal, aggregate, chemical, pharmaceutical, food and beverage, and minerals processing technologies, and more particularly to "smart" turbidity sensing filter apparatus and methods thereof.

BACKGROUND OF THE INVENTION

Filter presses, sometimes called "plate-and-frame" filter presses, "membrane" filter presses, or "chamber" filter presses, have been around since the 19th century and are generally used for dewatering processes. They are used to make filter cake products from liquid-solid suspensions or slurries having a large liquid fraction. The solids within the suspensions or slurries typically do not dissolve in the liquid fraction and thus, they are carried in it. Filter presses separate the solids from the liquids, so that the useful part can be processed, packaged or delivered to the next step. One non-limiting example of a prior filter press may be seen in U.S. Pat. No. 5,368,751, which is hereby incorporated by reference.

Filter presses generally work in a "batch" manner. A large number of filter plate assemblies are supported on and are guided along a metal frame. The plurality of filter plate assemblies are forced together using large hydraulic rams, at which point a pump feeds slurry into individual filter chambers which are defined by cavities or recesses between and formed within the faces of each filter plate assembly. The liquid fraction of the slurry (i.e., filtrate) passes through filter cloth provided to each filter plate assembly and into a drainage system, while the solid fraction stays behind in the filter chambers. When the filtration cycle is complete, a batch of solid filtered material, called "filter cake" is produced. The stack of filter plate assemblies is opened, solids are removed from the filter chambers via any one or more of gravity, vibrating, shaking, and/or manual extractors, and then the stack of filter plate assemblies is re-clamped and the filtration cycle is repeated.

In many cases, if a filter cloth gets damaged, for instance by a tear, small hole, wear spot, a fold, or misalignment with the filter plate assembly, the filtrate exiting a particular filter plate assembly will eventually become turbid with solids and the filtering process will be compromised. Higher than allowable turbidity levels can negatively affect downstream processes such as those that use the filtrate in a recycle feed. Higher than allowable turbidity levels can also result in lost profits if the filter cake is the desirable product and a large amount of solids are being discarded with the filtrate. It is, therefore, important to make sure that filter cloths are always functioning properly and not damaged. However, in a conventional filter press having upwards of 150 filter plate assemblies or more, the task of determining which cloth(s) is damaged becomes an incredibly time-consuming task. Each plate typically has two filter cloths thereon, and it can take many hours to visually inspect them all. The small spacing between filter plate assemblies generally requires complete removal of the filter plate assemblies for inspection.

To overcome the above problems, all filter cloths are generally simultaneously replaced at routine predetermined maintenance intervals. While such practices might reduce the chances of filter cloth failure during operation, it is inefficient and costly. More scheduled maintenance time means less production time and reduced operation efficiency. Changing out filter cloths which may still have ample service life cuts into the user's profit margin.

OBJECTS OF THE INVENTION

It is, therefore, an object of the invention to provide an improved filter capable of maximizing useful filter cloth service life and cost efficiency.

It is another object of the invention to provide a method of monitoring individual filter cloth performance in order to prevent unnecessary discarding of filter cloths which would otherwise have ample service life remaining.

Yet another object of the invention is to minimize the scheduled and unscheduled maintenance time for filtering operations and maximize the operation time of filtration equipment at little capital cost to the end user.

Another object of the invention is to maximize the safety and performance of filter operations by eliminating the need to remove filter components to check for filter cloth damage.

Another object of the invention is to reduce labor, troubleshooting, and maintenance time.

Another object of the invention is to provide "smart", yet inexpensive disposable means for monitoring turbidity levels which will work in harsh environments.

It is another object of the invention to provide a system capable of monitoring even small differences in filtrate turbidity levels from one filter chamber to another in a filter press.

These and other objects of the invention will be apparent from the drawings and description herein. Although every object of the invention is believed to be attained by at least one embodiment of the invention, there is not necessarily any one embodiment of the invention that achieves all of the objects of the invention.

SUMMARY OF THE INVENTION

A filter press comprises a plurality of stackable filter plate assemblies, and at least one turbidity sensing module coupled to a first filter plate assembly within the plurality of stackable filter plate assemblies. The turbidity sensing module may be positioned between a filtrate drain opening that communicates with a filter chamber, and a filtrate port or discharge tube. The turbidity sensing module is provided in order to determine a level of turbidity of the filtrate exiting said first filter plate assembly, independently of the turbidity levels of filtrate exiting other filter plate assemblies.

In some embodiments, a plurality of turbidity sensing modules may be provided to the first filter plate assembly. In some embodiments, multiple filter plate assemblies within the plurality of stackable filter plate assemblies may each incorporate at least one turbidity sensing module. Turbidity sensing modules may comprise one or more optical emitters and optical detectors, and in some instances, the number of optical detectors may outnumber the number of optical emitters. Optical detectors may also be provided at different angles with respect to the optical emitters. The optical detectors are configured to measure and determine an amount of electromagnetic radiation delivered by each optical emitter. Signal information regarding the electromagnetic radiation may be delivered to an interface unit, which communicates with a control system and/or an alarm via a hard wired or wireless communication means. A turbidity measurement chamber intersecting a drain channel may be provided to the filter plate assembly which is sized to accept a turbidity sensing module and prevent optical emitters and optical detectors from causing excessive turbulent flow within streams of filtrate. Turbidity sensing modules may comprise a housing defining a circuitry enclosure, a circuit board, at least one optical emitter, at least one optical detector, and potting material encapsulating or otherwise protecting the circuit board within the housing. In some embodiments only a small portion of the optical emitters and detectors remain exposed.

A filter plate assembly is also disclosed. The filter plate assembly generally comprises at least one filtrate drain opening connecting a filter chamber to a filtrate port or discharge tube via a drain channel. At least one turbidity sensing module being operatively connected to said drain channel is provided with the filter plate assembly. In use, the turbidity sensing module is configured to measure and/or indicate turbidity levels of filtrate exiting the filter chamber of said filter plate assembly. In some embodiments, a plurality of turbidity sensing modules may be provided to the filter plate assembly.

A method of filtering slurry is also disclosed. The method comprises providing a filter, such as a filter press having a plurality of stackable filter plate assemblies, providing at least one turbidity sensing module having at least one optical emitter and at least one optical detector to a first filter plate assembly within the plurality of stackable filter plate assemblies, locating the at least one turbidity sensing module such that the at least one optical emitter and the at least one optical detector are configured to be at least partially exposed to a stream of filtrate exiting a filter chamber of the first filter plate assembly, emitting electromagnetic radiation from the at least one optical emitter, allowing a stream of filtrate to run between said at least one optical emitter and said at least one optical detector, and determining, by the amount of electromagnetic radiation received by the at least one optical detector, a turbidity level of the filtrate exiting said first filter plate assembly independently of turbidity levels of filtrate exiting other filter plate assemblies within the plurality of stackable filter plate assemblies. In some embodiments, an alarm is activated if the turbidity sensing module determines that a threshold turbidity level has been reached for a particular filter plate assembly. Activation of the alarm may comprise, for example, producing a light, producing a sound, providing an electric signal, providing a communication such as a character message, or providing instructions to a control system. In a preferred embodiment, the alarm may be deactivated after replacing, repairing, or re-configuring a filter cloth, for example, by positioning a magnetic reset wand adjacent to the affected turbidity sensing module. Optical emitters described may be a light-emitting diode, wherein the step of emitting electromagnetic radiation comprises emitting light waves having wavelengths within the visible and/or invisible color spectrum. In some embodiments, certain properties of the optical emitters and optical detectors (e.g., such as operational wavelength range) may be tailored and/or optimized to work best with particular filtrates and particulate suspended therein.

Also disclosed, is a retrofit unit for a filter plate assembly comprising a housing body, a connector for attaching the retrofit unit to portions of the filter plate assembly, at least one drain channel configured to communicate with and receive filtrate from a filter chamber of the filter plate assembly, and, a turbidity sensing module operatively connected to the at least one drain channel.

BRIEF DESCRIPTION OF THE DRAWINGS

FIG. 5 is a detailed view showing the particulars of a third turbidity sensor arrangement;

FIG. 6 is a detailed view showing the particulars of a fourth turbidity sensor arrangement;

DETAILED DESCRIPTION OF THE INVENTION

Figure 1:
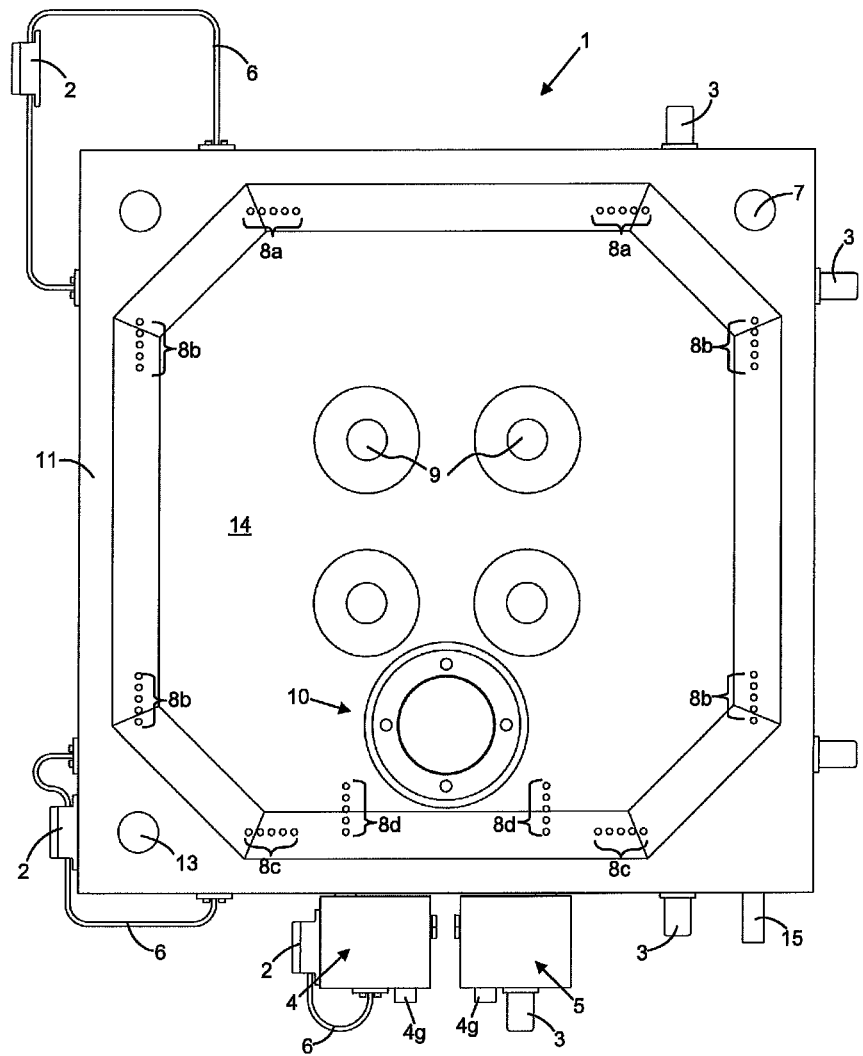
FIG. 1 illustrates a frontal view of first filter plate assembly according to some embodiments.
Figure 2:
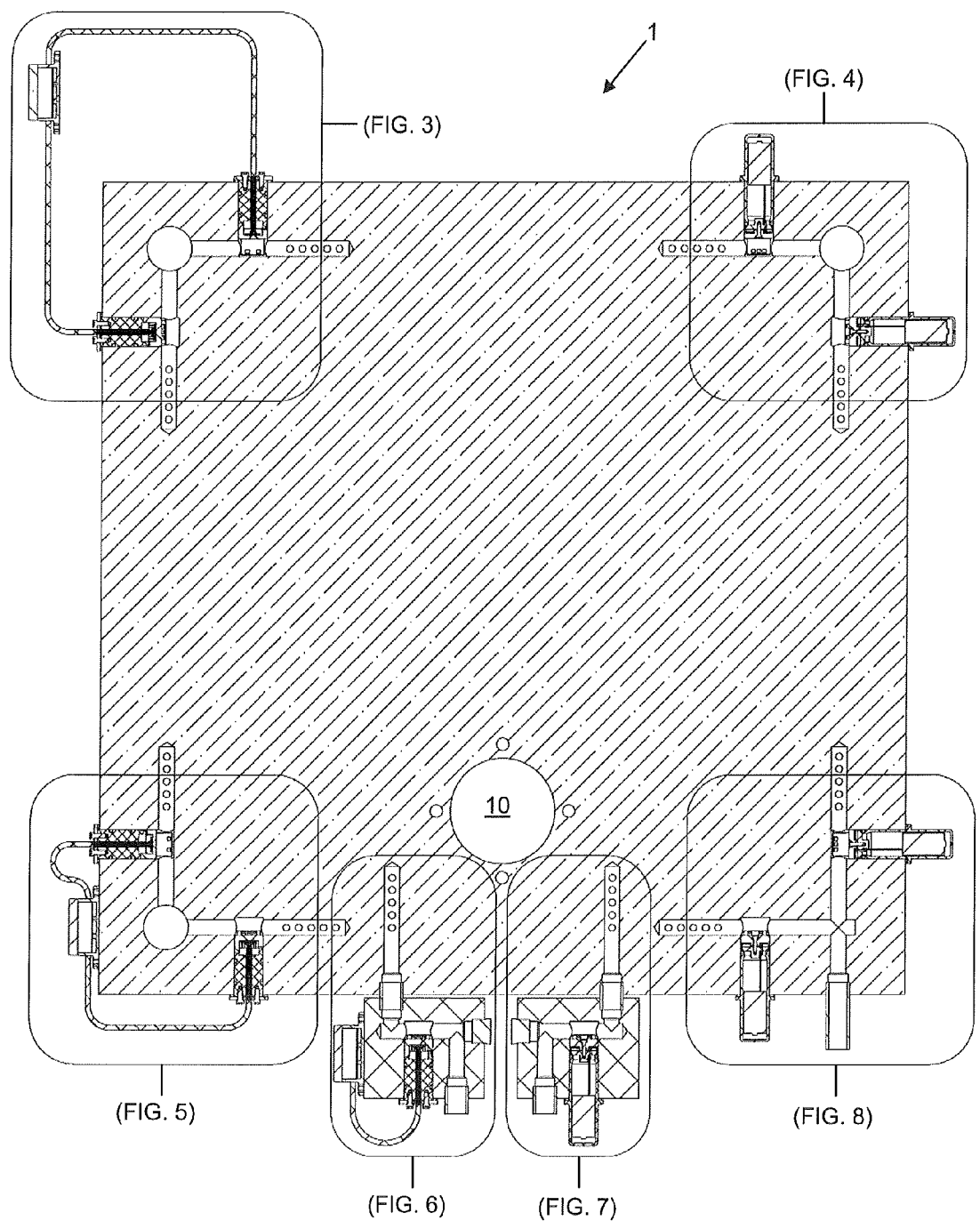
FIG. 2 is a frontal cross-sectional view of the first filter plate assembly shown in FIG. 1.

FIG. 1 illustrates a frontal view of a first filter plate assembly according to some embodiments. The filter plate assembly 1 comprises a peripheral sealing surface 11 surrounding a filter chamber 14 which may be configured to accept a filter cloth, screen, or other form of filtration media. One or more stay bosses 9 are provided within the filter chamber 14, which provide support during plate stacking. The filter plate assembly 1 further comprises a feed eye 10 for slurry infeed, and at least one of an upper filtrate port 7, a lower filtrate port 13, or a filtrate discharge tube 4g, 15. The filter plate assembly 1 may comprise at least one or more upper filtrate drain openings 8a, side filtrate drain openings 8b, lower filtrate drain openings 8c, or inboard filtrate drain openings 8d. In some configurations, the filter plate assembly 1 may comprise one or more external modules 2 connected to cables 6, one or more lower profile integral modules 3, or one or more retrofit units 4, 5 as will be discussed in further detail hereinafter.

Figure 3:
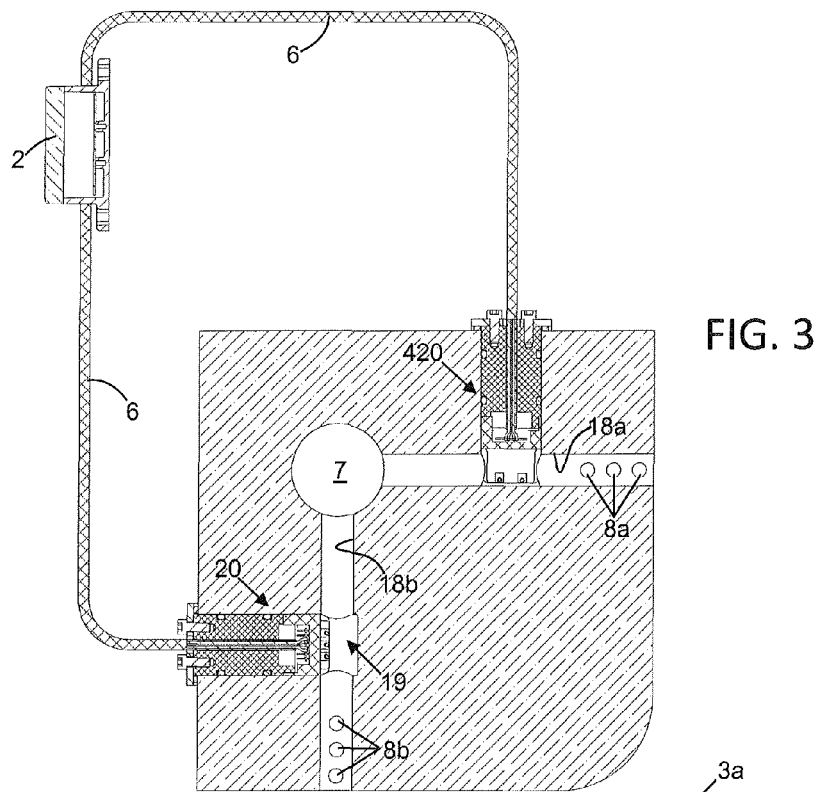
FIG. 3 is a detailed view showing the particulars of a first turbidity sensor arrangement according to FIG. 2.

FIG. 3 is a detailed view of a first turbidity sensor arrangement according to the invention. An upper drain channel 18a and a side drain channel 18b intersect at an upper filtrate port 7. A plurality of upper filtrate drain openings 8a and side filtrate drain openings 8b allow the upper 18a and side 18b drain channels to communicate with the filter chamber 14. A deep turbidity sensing module 420 may be provided from an upper portion of filter plate assembly 1. Sensing portions of the deep turbidity sensing module 420 are extended from the deep turbidity sensing module 420 so as to enable the measurement of turbidity level at bottom portions of the upper drain channel 18a. In this way, the turbidity of filtrate 50 flowing through upper drain channel 18a may be measured more accurately and without negative effects from bubbles, air, splashing, and turbulent flow which may be present at upper portions of the upper drain channel 18a. One or more external modules 2 may be operatively connected to the deep turbidity sensing module 420 via cables 6. A module 2 may, as shown, be mounted remotely from the filter plate assembly 1 at any convenient place, for example, on filter plate assembly supporting arms, sprayer bars, etc. In the particular embodiment shown, a single external module 2 is shared between multiple turbidity sensing modules 20, 420. While not shown, each turbidity sensing module 20, 420 may communicate with its own external module 2. Furthermore, while also not shown, each turbidity sensing module 20, 420 may be configured to communicate with multiple external modules 2 using hard wired 91, 93, 95 or wireless 90, 92, 94 communication means (see FIG. 13).

In some embodiments, a shallow turbidity sensing module 20 may be provided from a side portion of filter plate assembly 1 and disposed within a turbidity measurement chamber 19 intersecting the side drain channel 18b. As shown, sensing portions of the shallow turbidity sensing module 20 may be located more proximally to the module 20, as compared to the deep turbidity sensing module 420. In this regard, turbidity measurements are possible in various locations of the filter plate assembly 1 where there is less chance of disruption in flow that could negatively affect turbidity measurement.

Figure 4:
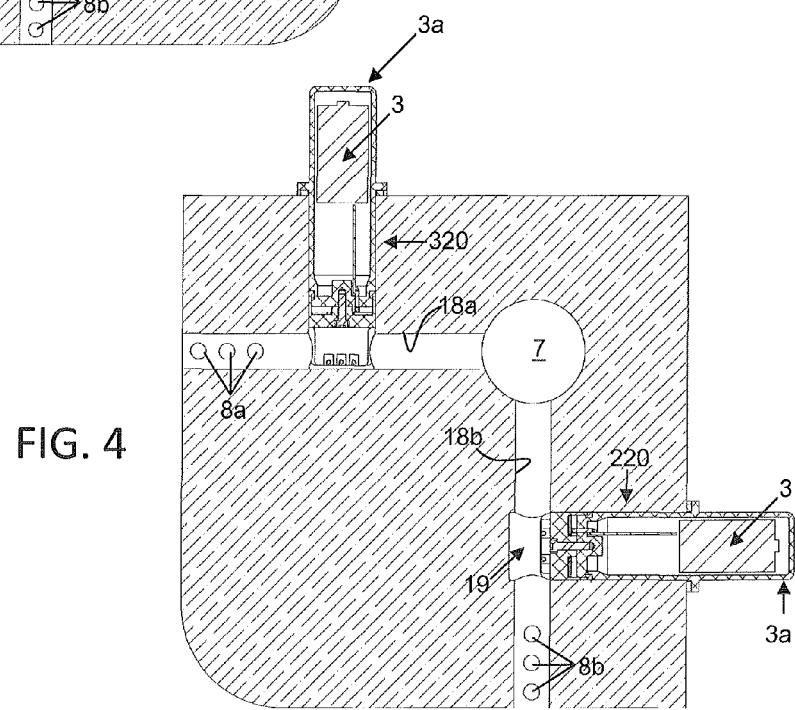
FIG. 4 is a detailed view showing the particulars of a second turbidity sensor arrangement.

FIG. 4 is a detailed view of a second turbidity sensor arrangement according to the invention. An upper drain channel 18a and a side drain channel 18b intersect at an upper filtrate port 7. A plurality of upper filtrate drain openings 8a and side filtrate drain openings 8b allow the upper 18a and side 18b drain channels to communicate with the filter chamber 14. A deep turbidity sensing module 320 may be provided from an upper portion of filter plate assembly 1. Sensing portions of the deep turbidity sensing module 320 are extended so as to measure turbidity at bottom locations within the upper drain channel 18a. In this way, the turbidity of filtrate 50 flowing through upper drain channel 18a may be measured more accurately and without negative effects from bubbles, air, splashing, and turbulent flow. One or more integral modules 3 may be operatively connected to the deep turbidity sensing module 320 without any necessary external cables 6. The integral module 3 may, as shown, be mounted so as to extend from the filter plate assembly 1 at a convenient place, for example, an upper portion of the filter plate assembly 1 which is easily viewable from the side of the filter press. Circuitry may be shared between the deep turbidity sensing module 320 and the integral module 3 so as to reduce the profile of and simplify the overall construction of the filter plate assembly 1. An outer at least partially translucent or transparent casing 3a may be provided around the integral module 3 to protect it and the deep turbidity sensing module 320. As shown, in some embodiments, the casing 3a may form part of the housing or body of the deep turbidity sensing module 320. While not shown, the integral module 3 may be partially or completely recessed within outer portions of the filter plate assembly if space limitations preclude the option of a highly visible protruding integral module 3.

In some embodiments, a shallow turbidity sensing module 220 may be provided from a side portion of filter plate assembly 1 and disposed within a turbidity measurement chamber 19 intersecting the side drain channel 18b. Sensing portions of the shallow turbidity sensing module 220 may be located more proximally as compared to the deep turbidity sensing module 320 as previously mentioned. In this regard, turbidity measurements may be made in various locations of the filter plate assembly 1.

Turning now to FIG. 5, a third turbidity sensor arrangement is shown. A lower drain channel 18c and a side drain channel 18b intersect at a lower filtrate port 13. A plurality of lower filtrate drain openings 8c and side filtrate drain openings 8b allow the lower 18c and side 18b drain channels to communicate with the filter chamber 14. A shallow turbidity sensing module 20 may be provided in a turbidity measurement chamber 19 extending into a lower portion of filter plate assembly 1. Sensing portions of the shallow turbidity sensing module 20 are located near the bottom of lower drain channel 18c where there is less chance of disruptions in flow that could negatively affect turbidity measurement. In this way, the turbidity of filtrate 50 flowing through lower drain channel 18c may be measured more accurately and without negative effects from bubbles, air, splashing, and turbulent flow which may be present in upper portions of the lower drain channel 18c.

Figure 9:
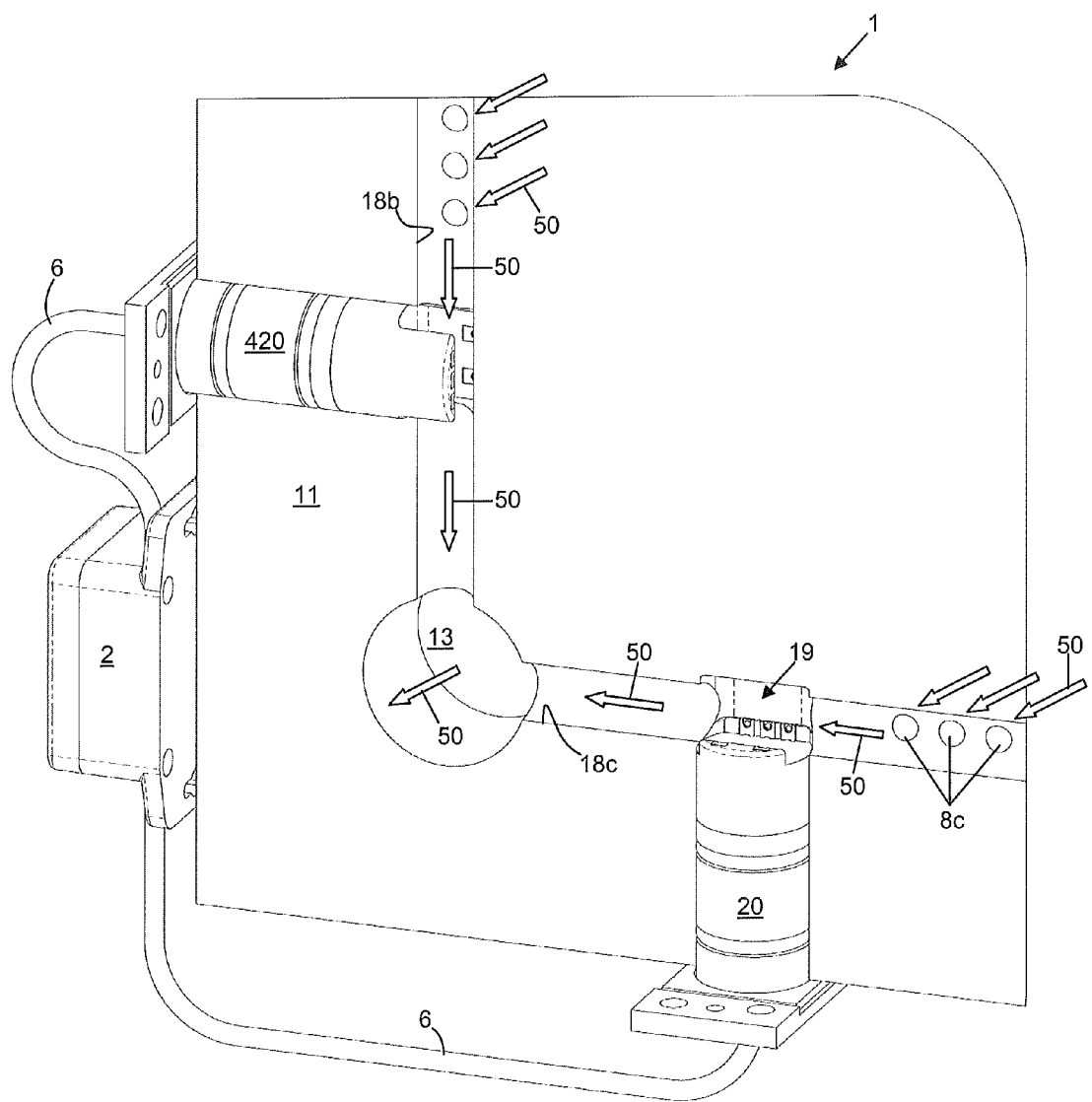
FIG. 9 is an isometric partial cutaway view of the third turbidity sensor arrangement shown in FIG. 5 showing the migration and egress of filtrate.

In a fashion similar to the first turbidity sensing arrangement shown in FIG. 3, an external module 2 may be shared between a deep turbidity sensing module 420 and shallow turbidity sensing module 20. For convenience, the external module 2 may be visibly mounted to a corner portion of the filter plate assembly 1 as shown for easy access. Rather than the shallow turbidity sensing module 20 used in the first turbidity sensing arrangement of FIG. 3, a deep turbidity sensing module 420 may be utilized with a side drain channel 18b as shown in FIG. 5. As previously mentioned, while not shown, each turbidity sensing module 20, 420 may communicate with its own external module 2. Furthermore, while not shown, each turbidity sensing module 20, 420 may communicate with multiple external modules 2. FIG. 9 is a cross sectional view of the filter plate assembly 1 which shows migration and egress of filtrate 50 as it moves through the third turbidity sensor arrangement of FIG. 5.

FIG. 6 is a detailed view showing a fourth turbidity sensor arrangement according to the invention. A first retrofit unit 4 is operably connected at a lower portion of the filter plate assembly 1 via a connector 4e. The first retrofit unit 4 comprises a housing body 4a, a transverse drain channel 4b, a lower vertical drain channel 4c, and an upper vertical drain channel 4d. A turbidity measurement chamber 19 intersecting the transverse drain channel 4b houses a shallow turbidity sensing module 20. The shallow turbidity sensing module 20 communicates with an external module 2 attached to the outside of the housing body 4a. The external module 2 is preferably oriented in a manner which provides clearance with trap doors or other conceivable mechanisms which are positioned proximately below the filter press plate stack. The external module 2 is also preferably oriented in a manner which provides easy visual and physical access to the module for software updates, alarm resets, routine maintenance, cleaning, removal, and replacement.

A plug 4f at one end of the transverse drain channel 4b may be provided to the first retrofit unit 4 in order to reduce costs and facilitate manufacturing of the transverse drain channel 4b. In use, filtrate 50 leaves the filter chamber 14 and enters one or more inboard filtrate drain openings 8d. The filtrate 50 travels through an inboard drain channel 18d and subsequently enters the upper vertical drain channel 4d via connector 4e. The filtrate continues to flow through the transverse drain channel 4b and then down through the lower vertical drain channel 4c before exiting filtrate discharge tube 4g. The shallow turbidity sensing module 20, measures turbidity of the filtrate 50 passing through the first retrofit unit 4 as will be described in more detail hereinafter. It will be understood and appreciated by those having an ordinary skill, that while not shown, the shallow turbidity sensing arrangement 20 may instead be oriented at an angle (e.g., 90 degrees) with respect to what is shown. For example, the turbidity measurement chamber 19 may extend diagonally or generally perpendicularly into the upper vertical drain channel 4d or the lower vertical drain channel 4c. In such alternative embodiments, the external module 2 may be positioned on a bottom portion of the housing body 4a, and the turbidity sensing module 20 may be provided at a side portion of the housing body 4a.

Figure 7:
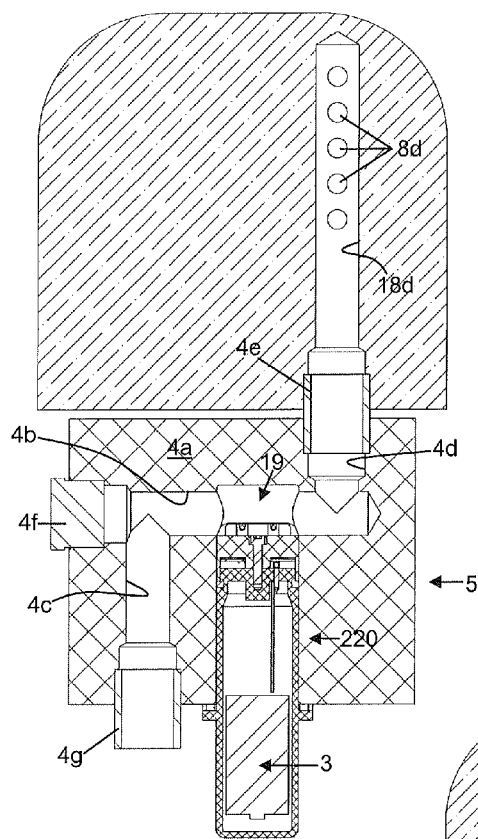
FIG. 7 is a detailed view showing the particulars of a fifth turbidity sensor arrangement.

FIG. 7 is a detailed view showing a fifth turbidity sensor arrangement according to the invention. The arrangement comprises a second retrofit unit 5 communicating with an inboard drain channel 18d. The second retrofit unit 5 is similar to the first retrofit unit 4 shown in FIG. 6. However, the second retrofit unit 5 differs from the first retrofit unit 4, in that it comprises a shallow turbidity sensing module 220 having an integral module 3, rather than an external module 2 connected by one or more cables 6. In the particular embodiment shown, the second retrofit unit 5 is mounted to the rest of the filter plate assembly 1 in an opposite orientation of what is shown for the first retrofit unit 4 in FIG. 6. It will be readily understood that the second retrofit unit 5 could alternatively be mounted in the same orientation as what is shown in FIG. 6. Moreover, while not shown, the shallow turbidity sensing arrangement 220 may instead be oriented at an angle (e.g., 90 degrees) with respect to what is shown. For example, the turbidity measurement chamber 19 may extend diagonally or generally perpendicularly into the upper vertical drain channel 4d or the lower vertical drain channel 4c. Furthermore, while not shown, the integral module 3 may be partially or completely recessed within outer portions of the housing 4a if space limitations preclude the option of a highly visible protruding integral module 3.

Figure 8:
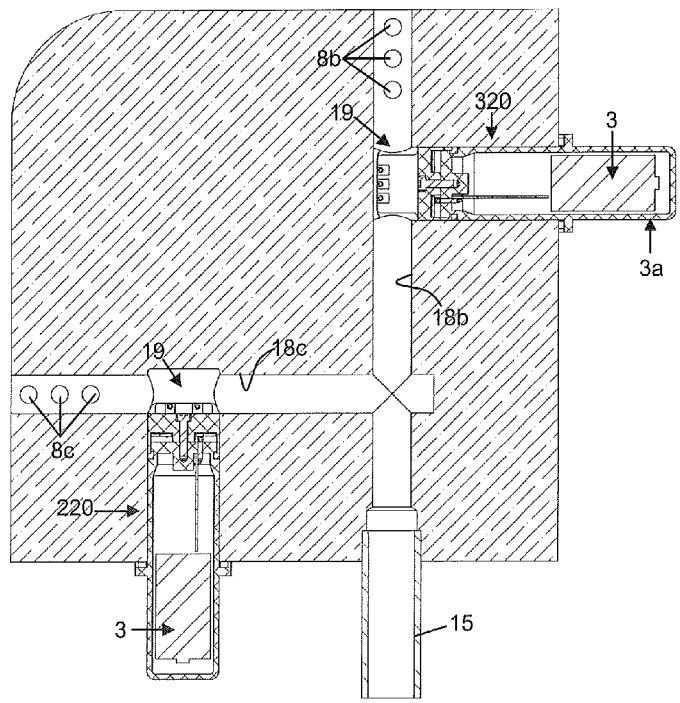
FIG. 8 is a detailed view showing the particulars of a sixth turbidity sensor arrangement.

FIG. 8 is a detailed view showing a sixth turbidity sensor arrangement according to the invention. A lower drain channel 18c and a side drain channel 18b intersect, allowing filtrate 50 to discharge from a filtrate discharge tube 15. A plurality of lower filtrate drain openings 8c and side filtrate drain openings 8b allow the lower 18c and side 18b drain channels to communicate with the filter chamber 14. A deep turbidity sensing module 320 may be provided from a side portion of filter plate assembly 1. One or more integral modules 3 may be operatively connected to the deep turbidity sensing module 320 without the need for the use of external cables 6. The integral module 3 may, as shown, be mounted so as to extend from the filter plate assembly 1 at a convenient place, for example, a side portion of the filter plate assembly 1 which is easily viewable from the side of the filter press. Alternatively, the integral module may be provided within a recessed portion or cavity of the filter plate assembly for a lower profile. Circuitry may be shared between the deep turbidity sensing module 320 and the integral module 3 so as to reduce the profile of and simplify the overall construction of the filter plate assembly 1. An outer at least partially translucent or transparent casing 3a may be provided around the integral module 3 to protect it and the deep turbidity sensing module 320. As shown, in some embodiments, the casing 3a may form part of the housing or body of the deep turbidity sensing module 320.

In some embodiments, a shallow turbidity sensing module 220 may be provided from a lower portion of filter plate assembly 1 and disposed within a turbidity measurement chamber 19 intersecting the lower drain channel 18c. Sensing portions of the shallow turbidity sensing module 220 may be located at lower portions of lower drain channel 18c where there is less chance of disruptions like bubbles, air, splashing, or turbulent flow which could negatively affect turbidity measurement.

Figure 10:
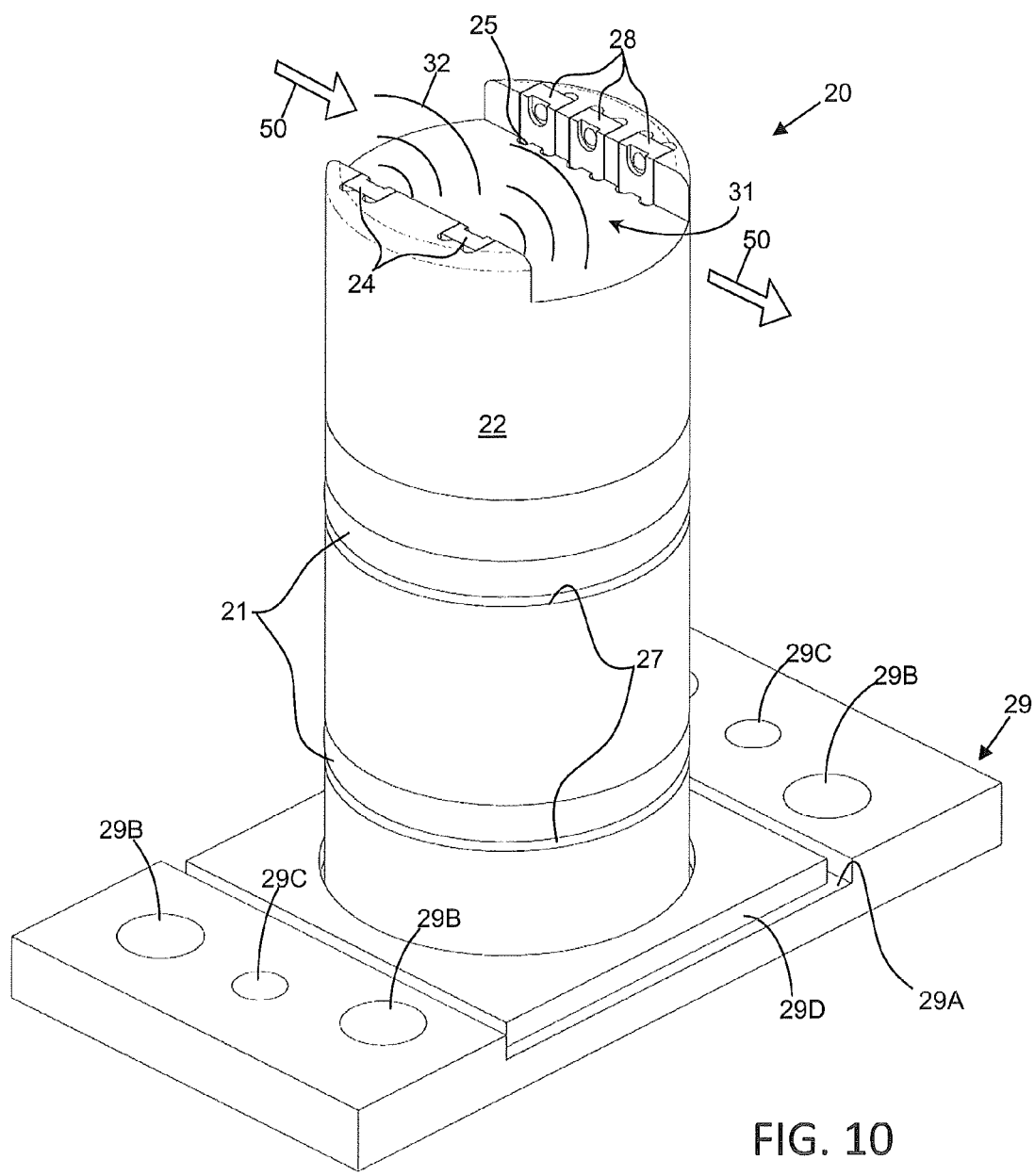
FIG. 10 is an isometric view of a shallow turbidity sensing module according to some embodiments.

FIG. 10 is an isometric view of a shallow turbidity sensing module 20 according to some embodiments. The shallow turbidity sensing module 20 comprises a housing 22 securable within a filter plate assembly 1, one or more mounting features such as a mounting plate 29, and sealing means such as one or more o-rings 21 disposed in one or more grooves 27 in the housing 22 or at least one gasket 29d provided within a holding portion 29a. In some embodiments, the holding portion 29a may comprise a recess, pocket, channel, annular groove, or the like. In other embodiments, the holding portion 29a may be a flat or lapped face capable of providing a seal. The mounting plate 29 may comprise one or more mounting holes 29b and one or more threaded holes 29c configured for receiving a removal jackscrew (not shown). Over time, gasket 29d and or o-rings 21 may become stuck to portions of the filter plate assembly 1, or a shallow turbidity sensing module 20 may become encrusted within a filter measurement chamber 19. By threading one or more removal jackscrews into the one or more threaded holes 29c, the mounting plate 29 and housing 22 may be easily dislodged from the rest of the filter plate assembly 1 via mechanical advantage.

Turbidity sensing module 20 comprises at least one optical emitter 24, 24a, 24b and at least one optical detector 28, 28a, 28b, 28c. The optical emitters 24, 24a, 24b are capable of emitting electromagnetic radiation 32, including one or more of the visible, infrared, full spectrum, UVC, UVA, UVB wavelengths, and may comprise, for example, filaments, bulbs, lasers, fiber optics, and/or light emitting diodes (LEDs). The optical detectors 28, 28a, 28b, 28c may comprise, for instance, one or more radiometers, photometers, photodetectors, photonic detectors, photovoltaics, photoconductive detectors, phototransistors, photodiodes, or the like. Optical emitters 24 and optical detectors 28 may comprise sealed protective windows, such as optically transparent or translucent glass or polymer panes or clear coatings which may serve to protect the emitters and detectors from damage (e.g., abrasion). Preferably, the optical emitters 24, 24, 24b produce one or more wavelengths which strategically complement the color, % volume of solids, solid properties, fluid properties, and light absorption characteristics of the filtrate being produced by the filter plate assembly 1. Also preferably, the optical detectors 28 have a greater sensitivity to those wavelengths which strategically complement the color, % volume of solids, solid properties, fluid properties, and light absorption characteristics of the filtrate being produced by the filter plate assembly 1. In this way, a diagnostic "sweet spot" is used for the turbidity measurement. More than a single wavelength may be intermittently utilized (e.g., multicolor L.E.D.) in order to cover a broad spectrum of filtrates or filtrates containing an assortment of different particulate compositions with different light absorption properties. For example, a wavelength between yellow/green and red visible light may be emitted by the optical emitters 24, 24a, 24b for filtration processes which produce golden-colored ferric oxide filtrates. As another example, red or infrared light may be emitted by the optical emitters 24, 24a, 24b for dark heavy clay filtrates. The optical emitters 24, 24a, 24b and optical detectors 28, 28a, 28b, 28c may be connected (e.g., via soldering) to a common printed circuit board encapsulated within the housing 22 by protective potting material 25 having good dielectric properties. "Potting material" 25 as it is used throughout this specification and appended claims, may be any material which is suitable for encapsulating, protecting, or sealing (e.g., a caulking, expanding closed cell foam, or other fill material). Potting material 25 may also comprise properties which provide a resistance to abrasion, or are suitable for bonding protective wear plates thereto, including adhesives. Potting material may comprise any suitable durometer or property such as tensile strength or shear strength. Potting material may further comprise polymers such as hard plastics, epoxy resins, and rubbers. A gap 31 extends between the optical emitters 24 and optical detectors 28 to allow filtrate 50 to pass therebetween as will be discussed hereinafter. While not shown, one or more wear plates in the form of small abrasion-resistant disks, tiles, liners, liners, or coatings may be provided to the gap 31 in any conventional manner. In one non-limiting example, a wear plate constructed of a small tile of glass may be affixed to the turbidity sensing module 20 by potting material 25 or other adhesive applied to the housing 22.

Figure 11:
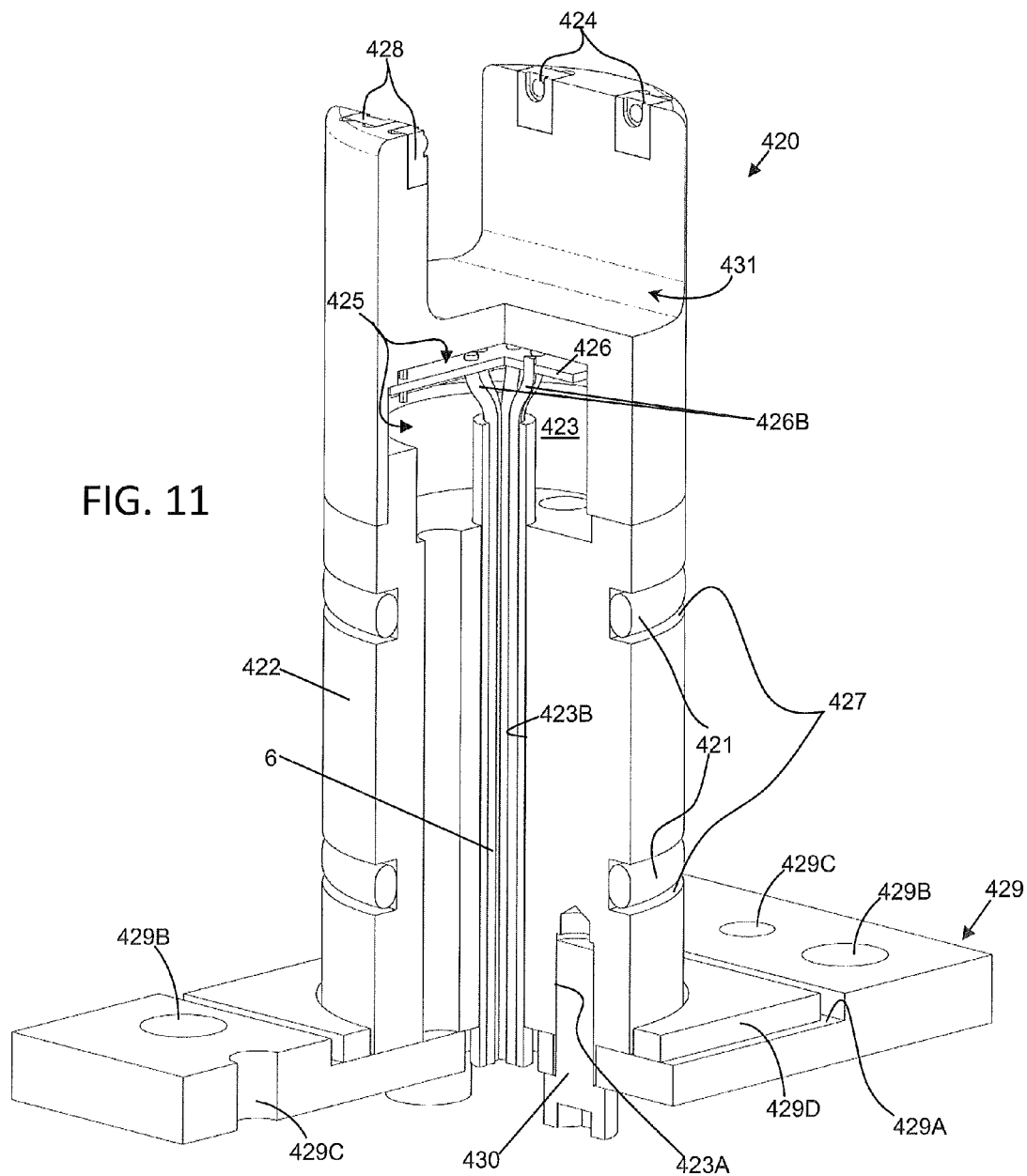
FIG. 11 is an isometric partial cutaway view of a deep turbidity sensing module according to some embodiments.

FIG. 11 is an isometric partial cutaway view of a deep turbidity sensing module 420 according to some embodiments. The deep turbidity sensing module 420 similarly comprises a housing 422 securable within a filter plate assembly 1, one or more mounting features such as a mounting plate 429, sealing means such as one or more o-rings 421 disposed in one or more grooves 427 in the housing 422 or at least one gasket 429d provided within a holding portion 429a. In some embodiments, the holding portion 429a may comprise a recess, pocket, channel, groove, flat sealing surface, or the like. The mounting plate 429 may comprise one or more mounting holes 429b and one or more threaded holes 429c configured for receiving a removal jackscrew (not shown). Over time, gasket 29d and or o-rings 421 may become stuck to other portions of the filter plate assembly 1, or the deep turbidity sensing module 420 may become encrusted within a filter measurement chamber 19. By threading one or more removal jackscrews, into the one or more threaded holes 429c, the mounting plate 429 and housing 422 may be easily dislodged from the filter plate assembly 1 via mechanical advantage.

Turbidity sensing module 420 comprises at least one optical emitter 424 and at least one optical detector 428. The optical emitters 424 may comprise, for instance, filament bulbs, lasers, fiber optics, or LEDs which emit electromagnetic radiation including one or more of the visible, infrared, full spectrum, UVC, UVA, UVB wavelengths. The optical detectors 428 may comprise, for instance, radiometers, photometers, photodetectors/photonic detectors, photovoltaics, photoconductive detectors, phototransistors, photodiodes, or the like. The optical emitters 424 and optical detectors 428 may be connected to a shared printed circuit board 426, which is encapsulated within a circuitry enclosure 423 with potting material 425. One or more wires 426b connected to the printed circuit board 426 form a cable 6 which may connect to an external 2 or integral 3 module. A gap 431 extends between the optical emitters and the optical detectors in order to allow filtrate 50 to pass therebetween as will be discussed hereinafter. A central opening 423B in the housing 422 may provide an opening for the cable 6 to pass. One or more lateral openings 423A may be provided in the housing 422 for attachment of the mounting plate 429 to the housing 422 using one or more fasteners 430. As shown, in some embodiments, the one or more fasteners 430 may comprise diametrically-opposed screws. In other embodiments, the one or more fasteners 430 may comprise, without limitation, rivets, welds, expanding fasteners, or adhesives such as industrial epoxies. While not shown, one or more wear plates in the form of small abrasion-resistant disks, tiles, liners, or coatings may be provided to the gap 431 in any conventional manner. In one non-limiting example, a wear plate constructed of a small tile of glass may be affixed to the turbidity sensing module 420 by potting material 425 or other adhesive applied to the housing 422.

Figure 12:
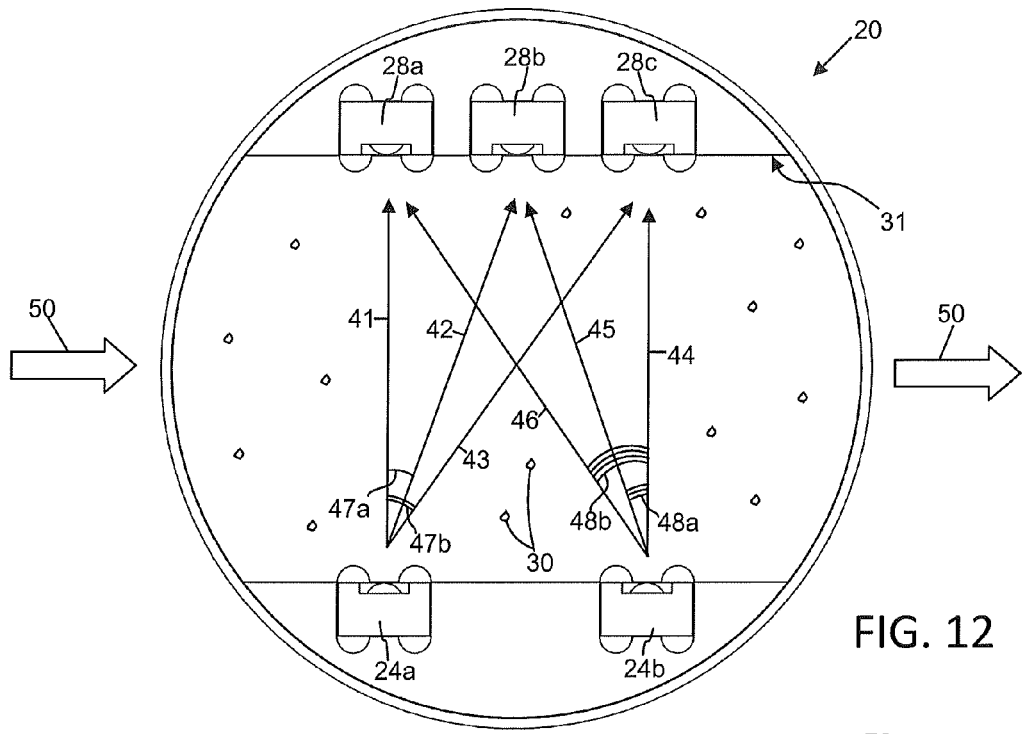
FIG. 12 is a schematic representation showing the function of a turbidity sensing module according to some embodiments.

FIG. 12 is a schematic representation showing the function of a turbidity sensing module according to some embodiments. When in use, filtrate 50 leaving the filter chamber 14 of a filter plate assembly 1 (and having an amount of particulate 30 suspended therein) enters a drain channel 18a-d and flows through the gap 31 separating the optical emitters 24a, 24b and optical detectors 28a, 28b, 28c. According to one exemplary and non-limiting embodiment, when a first optical emitter 24a and a second optical emitter 24b are off, a first voltage produced by a first optical detector 28a positioned in a first direction 41 with respect to the first optical emitter 24a may be recorded by a control system 70 in order to determine a baseline for dark noise at that particular location. Voltages may also be produced by second 28b and third 28c optical detectors which are positioned in second 42 and third 43 directions extending at first 47a and second 47b scatter angles, relative to the first direction 41, respectively. The voltage values from the second 28b and third 28c optical detectors may be recorded by a control system 70, in order to determine secondary baselines for dark noise at scatter angles 47a, 47b. Next, the first optical emitter 24a may be energized so as to emit electromagnetic energy 32 for a predetermined amount of time. A second voltage may be produced by the first optical detector 28a which is also recorded by the control system 70 in order to determine a primary baseline for direct light (when the first optical emitter 24a is on). Likewise, secondary voltages produced by the second 28b and third 28c optical detectors may be recorded by the control system 70 in order to determine baselines for indirect scattered light. When recording voltages, strategic "chopping" algorithms 108 may be employed by the control system 70 in order to accommodate various lag times, voltage ramp-ups, and voltage ramp downs.

Example 1

In some embodiments, all of the baselines for dark noise may be averaged together and all of the baselines for direct and indirect scattered light may be averaged together. Turbidity may be approximated as a function of total light absorption, wherein total light absorption is defined by the difference of the dark and light baseline averages as shown below.

When the first optical emitter 24a is off:
Recorded voltage @ $28a = V_{dark28a}$
Recorded voltage @ $28b = V_{dark28b}$ Recorded voltage @ $28c = V_{dark28c}$ $$AVG_{dark} = (V_{dark28a} + V_{dark28b} + V_{dark28c})/3$$

Dark noise baseline average = $AVG_{dark}$
When the first optical emitter 24a is on:
  Recorded voltage @ $28a = V_{light28a}$.
  Recorded voltage @ $28b = V_{light28b}$
  Recorded voltage @ $28c = V_{light28c}$ $$AVG_{light} = (V_{light28a} + V_{light28b} + V_{light28c})/3$$

Light baseline average for first optical emitter $24a = AVG_{light}$
Total light absorption = $AVG_{light} - AVG_{dark}$,
  where instantaneous turbidity 604 = f(Total light absorption)

Example 2

The above steps may be practiced with a second optical emitter 24b spaced from the first optical emitter 24a, in order to provide backup redundancy, robustness, and/or accuracy in the turbidity sensing module 20. For example, when the first optical emitter 24a is off, the second optical emitter 24b may be energized so as to emit electromagnetic energy 32 for a predetermined amount of time. A third voltage of the third optical detector 28c, which is located a fourth direction 44 from the second optical emitter 24b, may be recorded by the control system 70 in order to determine a primary baseline for direct light (when the second optical emitter 24b is on). Likewise, tertiary voltages produced by the second 28b and first 28a optical detectors may be recorded by the control system 70 in order to determine baselines for indirect scattered light at fourth 45 and fifth 46 directions extending at third 48a and fourth 48b angles, respectively.

When the first 24a and second 24b optical emitters are off:
  Recorded voltage @ $28a = V_{dark28a}$
  Recorded voltage @ $28b = V_{dark28b}$
  Recorded voltage @ $28c = V_{dark28c}$ $$AVG_{dark} = (V_{dark28a} + V_{dark28b} + V_{dark28c})/3$$

Dark noise baseline average = $AVG_{dark}$
When the first emitter 24a is on and the second 24b optical emitter is off:
  Recorded voltage @ $28a = V_{light28a1}$
  Recorded voltage @ $28b = V_{light28b1}$
  Recorded voltage @ $28c = V_{light28c1}$
When the first emitter 24a is off and the second 24b optical emitter is on:
  Recorded voltage @ $28a = V_{light28a2}$
  Recorded voltage @ $28b = V_{light28b2}$
  Recorded voltage @ $28c = V_{light28c2}$ $$AVG_{light} = (V_{light28a1} + V_{light28b1} + V_{light28c1} + V_{light28a2} + V_{light28b2} + V_{light28c2})/6$$

Light baseline average for both optical emitters 24a & $24b = AVG_{light}$
Total light absorption = $AVG_{light} - AVG_{dark}$,
  where instantaneous turbidity 604 = f(Total light absorption)

Example 3

Figure 16:
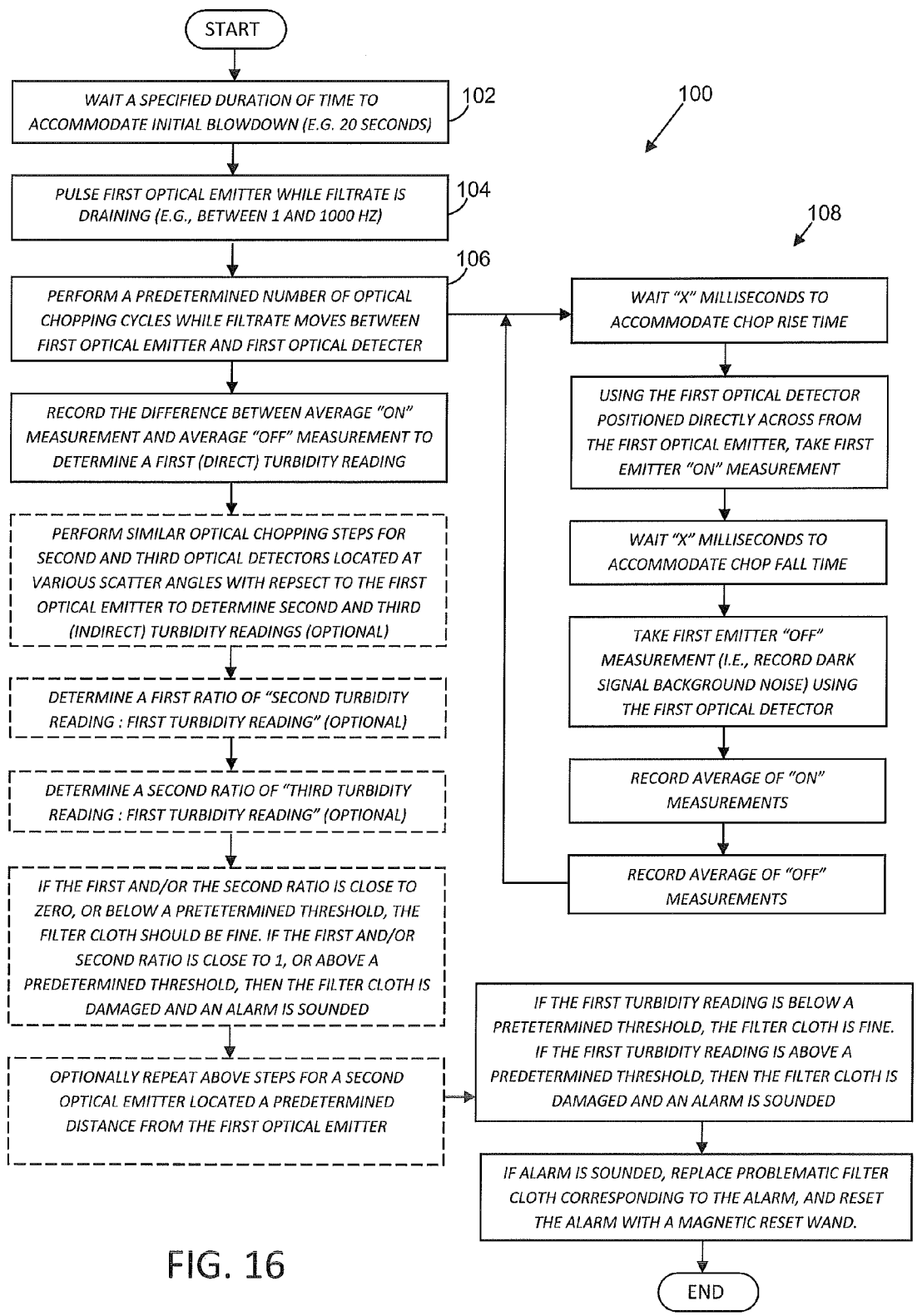
FIG. 16 illustrates a method of determining the condition of a filter cloth according to some embodiments.

Even more alternatively, and as will be apparent from the method 100 schematically shown in FIG. 16, the optical emitters 24a, 24b may, in some embodiments, intermittently pulse 104 at one or more predetermined frequencies (e.g., between approximately 1 Hz to 1000 Hz) for a number of times during each one of many measurement cycles over the course of a filtration cycle. The pulsing step 104 may be utilized to obtain a more accurate representation of instantaneous turbidity 604 of the filtrate 50 exiting the filter chamber 14. In other words, instantaneous turbidity 604 may be determined from an average of multiple very quick successive measurements. A single cycle of pulsing 104 may occur, for example, over the period of a fraction of a second (e.g., ¼ second) to approximate instantaneous turbidity 604 during said single cycle. Each pulse may last between a few milliseconds to a few hundred milliseconds. As visually depicted in FIG. 15, the pulsing cycles may occur between a time $t_2$ and $t_3$, after the filter chambers 14 are filled with slurry (between time $t_0$ and $t_1$), and after initial blowdown 102 when filtrate turbidity is highest (between time $t_1$ and $t_2$). Ratios of averaged voltage readings between each of the optical detectors 28a, 28b, 28c may be recorded and used by the control system 70 as shown below.

When first 24a and second 24b optical emitters are off, record N dark noise readings:
  Recorded voltages @ $28a = [V_{dark28a1}, V_{dark28a2}, V_{dark28a3}, \ldots V_{dark28aN}]$
  Recorded voltages @ $28b = [V_{dark28b1}, V_{dark28b2}, V_{dark28b3}, \ldots V_{dark28bN}]$
  Recorded voltages @ $28c = [V_{dark28c1}, V_{dark28c2}, V_{dark28c3}, \ldots + V_{dark28cN}]$ $$AVG_{dark28a} = (V_{dark28a1} + V_{dark28a2} + V_{dark28a3} \ldots + V_{dark28aN})/N$$

$$AVG_{dark28b} = (V_{dark28b1} + V_{dark28b2} + V_{dark28b3} \ldots + V_{dark28bN})/N$$

$$AVG_{dark28c} = (V_{dark28c1} + V_{dark28c2} + V_{dark28c3} \ldots + V_{dark28cN})/N$$

When first emitter 24a is on and second 24b optical emitter is off, record N light readings:
  Recorded voltages @ $28a = [V1_{light28a1}, V1_{light28a2}, V1_{light28a3} \ldots V1_{light28aN}]$
  Recorded voltages @ $28b = [V1_{light28b1}, V1_{light28b2}, V1_{light28b3} \ldots V1_{light28bN}]$
  Recorded voltages @ $28c = [V1_{light28c1}, V1_{light28c2}, V1_{light28c3} \ldots V1_{light28cN}]$ $$AVG1_{light28a} = (V1_{light28a1} + V1_{light28a2} + V1_{light28a3} \ldots + V1_{light28aN})/N$$

$$AVG1_{light28b} = (V1_{light28b1} + V1_{light28b2} + V1_{light28b3} \ldots + V1_{light28bN})/N$$

$$AVG1_{light28c} = (V1_{light28c1} + V1_{light28c2} + V1_{light28c3} \ldots + V1_{light28cN})/N$$

Average first emitter 24a direct light absorption = $AVG1_{light28a} - AVG_{dark28a} = AVG_{direct24a}$
Average first scatter absorption = $AVG1_{light28b} - AVG_{dark28b} = AVG_{scatter24a1}$
Average second scatter absorption = $AVG1_{light28c} - AVG_{dark28c} = AVG_{scatter24a2}$
First scatter ratio of first emitter $24a = AVG_{scatter24a1} / AVG_{direct24a} = R1_{24a}$
Second scatter ratio of first emitter $24a = AVG_{scatter24a2} / AVG_{direct24a} = R2_{24a}$
When first emitter 24a is off and second 24b optical emitter is on, record N light readings:
  Recorded voltages @ $28a = V2_{light28a1}, V2_{light28a2}, V2_{light28a3} \ldots V2_{light28aN}$
  Recorded voltages @ $28b = V2_{light28b1}, V2_{light28b2}, V2_{light28b3} \ldots V2_{light28bN}$
  Recorded voltages @ $28c = V2_{light28c1}, V2_{light28c2}, V2_{light28c3} \ldots V2_{light28cN}$ $$AVG2_{light28a} = (V2_{light28a1} + V2_{light28a2} + V2_{light28a3} \cdots + V2_{light28aN})/N$$

$$AVG2_{light28b} = (V2_{light28b1} + V2_{light28b2} + V2_{light28b3} \cdots + V2_{light28bN})/N$$

$$AVG2_{light28c} = (V2_{light28c1} + V2_{light28c2} + V2_{light28c3} \cdots + V2_{light28cN})/N$$

Average second emitter 24b direct light absorption=$AVG2_{light28a} - AVG_{dark28a} = AVG_{direct24b}$ Average third scatter absorption=$AVG2_{light28b} - AVG_{dark28b} = scatter24b1$ Average fourth scatter absorption=$AVG2_{light28c} - AVG_{dark28c} = AVG_{scatter24b2}$ First scatter ratio of second emitter 24b=$AVG_{scatter24b1}/AVG_{direct24b} = R1_{24b}$ Second scatter ratio of second emitter 24b=$AVG_{scatter24b2}/AVG_{direct24b} = R2_{24b}$ where Total light absorption=$f(AVG_{direct24a}, AVG_{direct24a}, R1_{24a}, R2_{24a}, R1_{24b}, R2_{24b})$ and instantaneous turbidity 604=f(Total light absorption)

Example 4

In a simple arrangement for measuring optical transmission through a filtrate 50, a single optical emitter 24 shines light directly towards a single optical detector 28, wherein the emitter 24 and detector 28 face each other across the flow of liquid filtrate 50 to be measured. The optical detector 28 signal indicates what fraction of the source illumination is transmitted through the filtrate 50 without being absorbed or angularly scattered away from the optical detector 28. This fraction may be defined as Transmission (T), which has a simple linear relationship with light intensity:

$$T = \frac{I}{I_0}$$

where $I_0$=initial intensity with no absorption, and I=measured intensity. Measured intensity I is generally between 0 and 1, or 0% and 100%). Transmission T is a ratio, and therefore, it is a dimensionless property. Transmission through clear filtrates 50 having no absorbing substances therein may use a reference point where T=1 (or 100%). When the optical path between the optical emitter 24 and optical detector 28 is so strongly absorbing that no light is received by the detector 28, then a reference point of T=0 (or 0%) may be used. The relationship between T and the amount of absorbing/scattering material blocking the path of light between the optical emitter 24 and the optical detector 28 generally follows the exponential Beer-Lambert Law:

$$T = \frac{I}{I_0} = e^{-kx}$$

where k=the absorption coefficient, and x=the optical path length between the optical emitter 24 and the optical detector 28. Since x is a measurement defined in units of length, k must also be defined in units of $$\frac{1}{length},$$

in order to be consistent with a dimensionless T ratio. With higher turbidity levels (i.e., dirtier filtrates 50 with more particulate 30), the value of k increases, and the value of T decreases. If the optical properties of the material contributing to turbidity are known a priori, then the length of optical path through the measurement chamber can be designed to optimize sensitivity and signal/noise. In such instances, the dimensions of gap 31, 431 may be customized for a specific filtering process, filtrate composition, and/or cake composition.

Optical emitters 24 may be energized continuously or may be selectively turned off between readings in order to reduce power consumption. In such embodiments, a signal produced by an optical detector 28 may be measured as often as desired, for example, only at times when an optical emitter 28 is energized. The light intensity may be held constant, based on the voltage and current provided to the optical emitter 28.

Such a basic measurement scheme may be used when simplicity and low cost are a high priority. However, such arrangements may have limitations. For example, ambient or stray light (light measured by an optical detector 28 that did not come from an optical emitter 24) may cause the system to be susceptible to inaccuracies. Second, such a system may not be able to clearly distinguish whether or not light removed from a direct path between the emitter 24 and the detector 28 was removed by absorption or by scattering (angular redirection). In some circumstances such distinctions can be important as will be discussed in more detail hereinafter. Third, such a basic measurement system lacks built-in accuracy checks, which can be useful in accounting for affects of "drift" and/or failure of electronic and optical components, etc.

Example 5

Refinements to improve measurement accuracy may be made according to the invention. Such improved implementations of turbidity sensing modules 20, 220, 320, 420 may reduce measurement error due to ambient stray light. Several methods may be used individually or in conjunction with each other, in order to improve accuracy.

In some embodiments, shielding may be provided to turbidity sensing modules. Shielding may be accomplished by optically sealing or otherwise covering the entire optical system with opaque materials in order to keep ambient light from entering the measurement system. The level of shielding may vary between a light shielding, and a near-perfect shielding.

Example 6

In some embodiments, a limited wavelength bandpass filter arrangement may be used with turbidity sensing modules disclosed herein. For example, optical emitters 24a, 24b and optical detectors 28a, 28b, 28c may be complimentarily matched together and tailored or engineered for best performance within a narrow range of wavelengths (i.e., colors). Such specific wavelength ranges may be referred to as the bandpass or passband bandwidth. In use, any stray light having a wavelength which fall outside of the bandpass/bandwidth may simply be ignored.

For broad-band optical emitters 24, such as incandescent lamps, bandpasses can be accomplished using an optical filter. Narrow-band optical emitters 24 such as light-emitting diodes (LEDs) and lasers are preferable over broad-band optical emitters 24, because they inherently emit light in narrow wavelength ranges. Moreover, LEDs are readily available with bandpasses of differing wavelengths and widths, depending on the solid-state technology used. Additionally, LEDs are inexpensive, versatile, and make great stable optical emitters 24 for the purposes and applications described herein.

Optical detectors 28 may incorporate many different electro-optical technologies; however, preferred embodiments include solid-state silicon-based photodetectors, which are generally inexpensive, versatile, stable, and a good match for LED optical emitters 24. Silicon photodetectors generally have broad-band wavelength sensitivity ranging from the near-UV or blue wavelengths (~350-400 nm) to near-infrared wavelengths (NIR, ~1000-1100 nm). The greatest sensitivity for silicon detectors is in the NIR, or between about 850 and 950 nm. In order to achieve a narrow bandpass with silicon detectors, an optical filter or other technological means for additional filtering may be required. The optical filter or other technological means for providing additional filtering may be incorporated directly into the optical detector 28 or indirectly applied to portions thereof. In some preferred embodiments where excessive filtering is unnecessary, a matched near-IR bandpass centered between approximately 850 and 950 nm may be used. Not only is this an efficient wavelength range for LED emitters 24 and silicon-based optical detectors 28, but many indoor lights, especially fluorescents, generally emit little or no competing energy in the near-infrared range.

Example 7

Another way to remove the effects of possible stray ambient light from optical measurements is through a technique known as "chopping". Here, separate rapid measurements are taken of the signal produced by an optical detector 24. The rapid measurements are taken both while an optical emitter 24 supplies light, and when the optical emitter 24 is not supplying light. The signals produced by the optical detectors 28 and measured while the emitters 24 are supplying light are generally referred to as light signals. Signals produced by the optical detectors 28 and measured while the optical emitters are off, blocked, or otherwise not producing light, are referred to as dark signals. Dark signals are generally due to noise or ambient sources of light other than the optical emitters. A simple mathematical subtraction for each measurement (e.g., light signal–dark signal) yields the desired, accurate, true signal or dark-corrected signal.

Chopping techniques such as those which incorporate a rotating mechanical slotted wheel to continuously alternate between letting light through and blocking it may be advantageously utilized. For example, a waterwheel-type mechanism (not shown) may be disposed within the gap 31, 431 between an emitter 24 and a detector 28. The waterwheel-type mechanism may rotate by virtue of hydraulic forces of filtrate 50 flowing through drain channels 18a-d and between gaps 31, 431 and may serve to optically chop optical detector measurements in order to obtain dark-corrected signals.

Alternatively, if solid-state devices such as LEDs are used for emitters 24, then electronic chopping may be performed by simply pulsing power to the emitter 24 on and off in rapid succession. It should be noted that optical emitters 24 and optical detectors 28 and their circuits may not respond "instantly" to abrupt changes in power or light signal, but may instead have capacitive time constants. Therefore, it is envisioned that the design of such devices which utilize chopping techniques will incorporate a chopping speed which is: A) fast enough to accurately correct for any time-varying stray light sources, but B) slow enough to allow the electro-optical components to stabilize for accurate readings.

By using inexpensive components such as LEDs and phototransistors, relatively slow chopping rates of a few hundred Hz or less may be utilized. Such rates are more than adequate for turbidity-measurement applications in filtration flowsheets.

Example 8

Through "absorption" and/or "scattering" phenomena, direct electromagnetic radiation 32 that is emitted from the optical emitters 24a, 24b, 24 in the form of concentrated light beams might be weakened prior to its detection by the optical detectors 28a, 28b, 28c. Absorption might occur when some of the light energy produced by an emitter 24 is absorbed by the filtrate 50 and/or particulate 30 passing by the emitter 24. Scattering may occur through a combination of reflection, refraction, and diffraction, where some of the light energy produced by an emitter 24 diffuses through the filtrate 50 and is changed by particulate 30 therein, e.g., in the form of solid suspended turbidity particulate 30 or immiscible liquid droplets. Common examples of scattering include the behavior of headlights in fog (water droplets suspended in air), blue sky (short wavelengths of light scattered by atmospheric molecules), and the milky appearance of water when mixed with a small amount of fine-grained white powder (e.g. flour, corn starch, clean mine tailings). Scattering is a complicated function of the wavelength, refractive index of the fluid, and properties of the particles of particulate 30, such as refractive index, absorbance, particle size and shape. In general, the following conditions favor more scattering: a) relatively transparent (non-absorbing) particles; b) particles with an index of refraction different from the surrounding fluid; c) particles that are smaller in size; and d) light that is of shorter wavelength.

Redirected light energy might not always be sensed by the optical detectors 28a, 28b, 28c, since it may follow other paths 42, 43, 46, 45 and angles 47a, 47b, 48a, 48b which stray beyond the original beam 41, 44 of electromagnetic radiation 32 and well outside the zone of detection of the optical detectors 28a, 28b, 28c. Depending on the optical properties of the particulate 30, measurements made by the turbidity sensing modules 20, 220, 320, 420 can often be improved by compensating for scattering by adding one or more "off-angle" optical detectors 28b, 28c in addition to a direct-beam optical detector 28a. The "off-angle" optical detectors measure scattering measure light at angles 47a, 47b outside the direct beam 41 from an optical emitter 24a.

In one instance, a single optical detector 28a may be placed in a first direction 41 which follows the direct line-of-sight path of a beam of electromagnetic radiation 32 leaving an optical emitter 24a. In other words, the detector 28a looks directly at or faces the optical emitter 28a. A second optical detector 28b may be positioned at one or more angles 47a with respect to the first direction 41. For example, the second optical detector 28b may be positioned at 90° (or perpendicular) with respect to the optical emitter 24a.

The ratio $$\frac{\text{side signal}}{\text{direct signal}}$$

may be obtained by recording signal measurements from the first optical detector 28a (direct signal) and the second optical detector 28b (side signal). Such a ratio is a fairly sensitive measure of the turbidity, and, because the result is ratiometric, it has the advantage of being insensitive to possible light-intensity variations from the optical emitter 24a. For a perfectly clear fluid with no turbidity, the first optical detector 28a will generally measure a strong signal, while the 90° second optical detector 28b will likely measure no signal. Therefore, the ratio will approach 0. As turbidity-causing contaminants are added, or as particulate 30 increases within the filtrate 50 due to failed filter cloths, progressively more light diffuses out from the direct beam 41, increasing the side signal at the expense of the direct signal, moving the ratio closer to 1.

However, the amount of scattering and the range of scattering angles 47a, 47b, 48a, 48b may be highly dependent on the absorbency or transparency of the particulate 30. In order to measure a significant side signal from an optical detector that is positioned 90° with respect to the first direction 41 of the emitter's direct beam, the average photon of light emitted might need to scatter off many different particles within the particulate 30, in order to randomize the angular distribution of energy ("multiple scattering"). In order for there to be a significant amount multiple scattering, the particulate 30 may need to be very transparent, such that the probability is low that a given photon will be absorbed in a given scattering event. If the particulate 30 is 1% absorbing (very transparent) then the average photon emitted from the optical emitter 24a might statistically survive nearly 70 scattering events without being absorbed, and light will be able to be redistributed over a broad range of angles. However, with particulate that is 10% absorbing (e.g., a fairly white powder) then the average photon emitted from the optical emitter 24a will generally survive only 7 scattering events, wherein the intensity of scattered light will be lessened with each scattering event and will be concentrated at angles closer to the direct beam 41 (so-called "forward scattering").

With highly absorbing particulate 30 such as carbon particulate, copper ore particulate, and molybdenum ore particulate, very little or essentially no scattering takes place. Most photons that hit the particulate 30 are generally absorbed and will not be detected by a second optical detector 24b at any angle 47a, 47b. Most photons that survive to be detected by the first optical detector 24a are likely ones that avoided hitting the particulate 30 in the first place, and these photons will follow the first direction 41 on their original path straight from the emitter 24a to the first detector 28a.

For these reasons, the turbidity sensing modules 20, 220, 320, 420 of the present invention may be optimally-designed for the specific characteristics of the particulate 30. In some instances, a turbidity sensing module may comprise a second optical detector 28b at 90° with respect to the first direction 41 where very light-colored, weakly absorbing particulate 30 is expected. Such configurations (not shown) may be particularly useful for food processing, waste-water treatment, and environmental water monitoring applications. Most geologic materials, however, have higher optical absorption, and therefore, exhibit reduced scattering and a dominance of forward scattering over side scattering. FIG. 12 shows a representative example of such a module designed with optimized turbidity-sensor geometries, wherein one or more optical detectors 28b, 28c measure scattered light at angles 47a, 47b, 48a, 48b which are smaller than 90° relative to the first 24a and/or second 24b optical emitters. Such smaller angles 47a, 47b, 48a, 48b may be, for instance, less than, slightly greater than, or equal to about 30°-45°.

Example 9

When used as optical emitters 24, LEDs may exhibit a statistical range of brightness efficiency from unit-to-unit, for a given electrical power. Similarly, silicon photo detectors may have unit-to-unit variations in their sensitivity. Such variances may be addressed by characterizing the combined response of every optical emitter/detector pair, and then "equalizing" the response. Response equalization may be accomplished, for example, using hardware (e.g. by adjusting the LED current for more or less light) or by using software (e.g., by numerically applying one or more stored correction factors to a given measurement). While such extraneous calibration steps might slightly increase the cost of the turbidity sensing modules 20, 220, 320, 420, they generally provide greater accuracy even when using cheap and highly variable components. The performance of turbidity sensing modules 20, 220, 320, 420 disclosed herein may be further improved by utilizing multiple optical emitters 24a, 24b and/or multiple optical detectors 28a, 28b, 28c. In this manner, redundancy may serve to improve reliability, especially with low cost un-calibrated optical emitter 24 and detector 28 components.

In one example, at least two independent optical emitters 24a, 24b and at least two optical detectors 28a, 28c may be provided to a turbidity sensing module 20 wherein each of the at least two optical detectors 28a, 28c are positioned in first 41 and fourth 44 directions. The first 41 and fourth 44 directions follow the direct line-of-sight paths of the electromagnetic radiation 32 leaving the at least two emitters 24a, 24b (i.e., there is no scattering in first 41 and fourth 44 directions). Independent measurements are taken through the same filtrate 50 with each coupled emitter/detector pair 24a, 28a; and 24b, 28c. The two results are then averaged, statistically reducing inaccuracies related to part-to-part variations described above. For many turbidity measurement applications, the resulting accuracy through averaging will be adequate to eliminate the need for custom calibration. A second benefit of using multiple optical emitters 24a, 24b, and multiple optical detectors is "error detection" and "redundancy". For example, if one optical emitter/detector pair 24a, 28a; or 24b, 28c consistently returns invalid results, or, if results from multiple optical emitter/detector pairs 24a, 28a; 24b, 28c disagree or extend outside of preset limits, a failure of the turbidity-sensing module 20 is detected. Upon detection of a failure, the module 20 may communicate an error condition that indicates a partial failure or total failure. Such communications may be wireless 94 or hard-wired 95 and may trigger appropriate corrective action (e.g., an alarm 80 indicating a need for replacing a turbidity-sensing module 20). If a partial failure is detected, another option might comprise communicating an error but still continue to provide turbidity data from the remaining optical emitter/detector pairs 24a, 28a; 24b, 28c. In some industrial applications, such communications 94, 95 might help distinguish between turbidity-sensing modules 20, 220, 320, 420 that need to be replaced on an urgent basis, and modules that may continue to be used until a more convenient time for replacement (e.g., during a scheduled routine maintenance period).

Example 10

A more sophisticated implementation which also incorporates scattering measurements may be alternatively be used, as shown explicitly in FIG. 12. A first measurement sequence uses a first emitter 24a as a light source. Intensity readings are taken in turn for optical detectors 28a, 28b, and 28c. In such an example, a first optical detector 28a is the direct beam 41 measurement device, while a second optical detector 28b detects low-angle forward scattering at an angle 47a, and a third optical detector 28c detects higher-angle forward scattering at an angle 47b. A second measurement sequence uses a second emitter 24b as a light source, where optical detector 28c is the direct beam 44 measurement, optical detector 28b measures low-angle forward scattering at an angle 48a, and optical detector 28a measures higher-angle forward scattering at an angle 48b. With perfectly accurate and calibrated components, these two mirror image measurement sequences might theoretically provide identical data. However, because the components used within the turbidity-sensing modules 20, 220, 320, 420 are not perfect and susceptible to unit-to-unit variation, a comparison of the mirror-image data and data ratios thereof may be used to improve accuracy and add redundancy to the system as described in the aforementioned paragraphs. Of course, it is anticipated that many other methodology refinements such as chopping (described in 2c, above) may be advantageously combined with these and other algorithms using multiple optical emitters 24 and detectors 28 in order to further improve measurement accuracy and consistency.

Example 11

Figure 17:
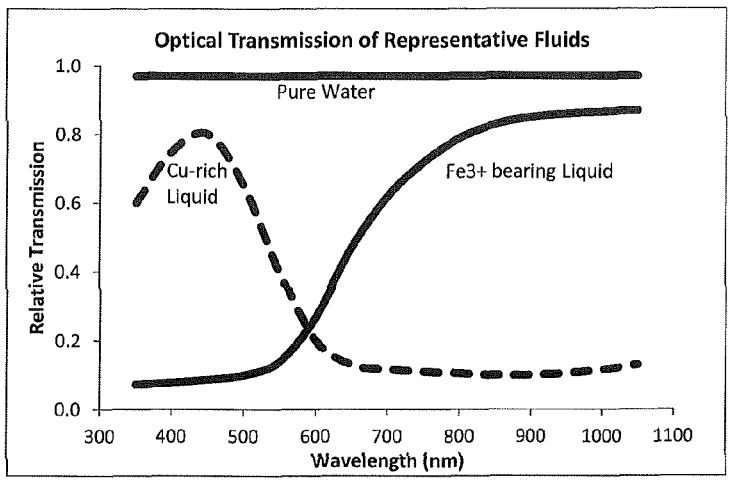
FIG. 17 graphically depicts optical transmission as a function of wavelength for various fluids.

Another unique feature of the present invention, is that depending on the coloration ("wavelength-dependent transmission/absorption") of the filtrate 50 and/or the turbidity-causing particulate 30, the operating wavelength of the optical emitters 24a, 24b and the optical detectors 28a, 28b, 28c can be judiciously chosen on a case-by-case basis, in order to optimize the sensitivity and accuracy of turbidity measurements. FIG. 17 shows schematic representations of spectra for three turbidity-free liquids. As shown, "Pure Water" has high optical transmission (low absorption) at all wavelengths in the visible and near-infrared (VNIR), and therefore, does not in and of itself dictate a specific wavelength range for optimal measurements. Accordingly, the turbidity-sensing modules defined herein comprise refinements which optimize performance by selecting an appropriate wavelength of light energy emitted by the optical emitters 24.

For example, copper-rich filtrates 50 comprised of water and a significant amount of dissolved copper (from the processing of copper ore) may comprise a visually transparent blue color. Therefore, optical emitters 24 and detectors 28 for use in processes involving copper rich filtrates 50 would best be chosen to operate in the blue or blue-green region (or between approximately 350 nm and 500 nm), where the fluid is most transparent. By comparison, optical emitters 24 and detectors 28 which operate purely in the red and near-infrared region (or between approximately 600 nm and 1050 nm) would likely not be suitable to use for such copper-rich filtrates, because most of the light produced by the emitters 24 would likely end up being absorbed by the liquid itself prior to detection by the optical detectors 28.

A different example of a strongly-colored filtrate 50 might include ferric oxide (Fe3+). Iron is very common in geologic materials, and ferric (oxidized) iron exhibits intense optical absorption at shorter visible wavelengths (e.g., blue and green). Visually, this leads to strong characteristic yellow, orange, rusty brown, and/or red colors. The best optical transmission through such a filtrate would, instead, be in the near-IR range (between approximately 800 nm and 1050 nm). Accordingly, for filtration processes involving ferric oxide filtrates 50, optical emitters 24 and detectors 28 would preferably favor this operating range for best turbidity sensing.

Figure 18:
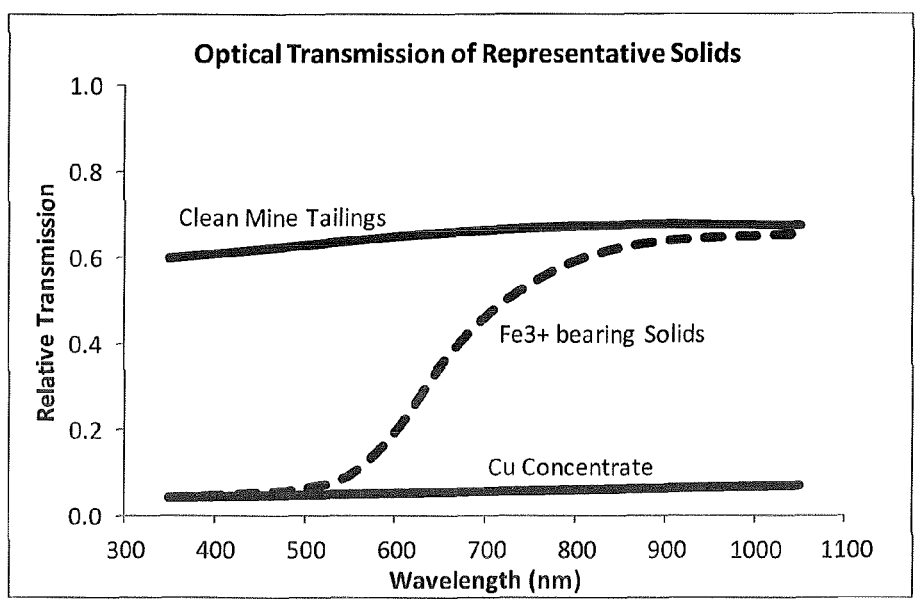
FIG. 18 graphically depicts optical transmission as a function of wavelength for various solids.

Contaminants and/or other particulate 30 that contribute to turbidity of a filtrate 50 can also have wavelength-dependent characteristics that come into play for optimization. For example, FIG. 18 shows schematic representations of spectra for three types of solids which are common in the mining industry:

"Cu Concentrate" is concentrated copper ore, which is primarily dark gray to black at all wavelengths in the visible and near-infrared (VNIR) wavelengths. Nearly all photons that interact with a particle of this material will be absorbed, and there will be very little scattering (as discussed above). Other materials with similar high absorption at VNIR wavelengths include carbon, coal, and molybdenum ore. None of these solids of themselves would dictate a particular wavelength for optimizing measurements.

"Clean Mine Tailings" represents fine-crushed rock (typically silicates and/or carbonates) which has been depleted of ore minerals during the refining process. In many instances, the optical transmission is much higher (and absorption much lower) than copper-concentrate; however, these optical properties do not vary much as a function of wavelength. In other words, materials like clean tailings do not strongly dictate an optimal operating wavelength based directly on transmission & absorption. Rather, the less absorbing the turbidity material is, the more prominent scattering will be, which can be used to good diagnostic benefit as discussed above.

"Fe3+ bearing Solids" represents a common class of particulate 30 having spectral characteristics of ferric oxide-bearing solids. In general, high concentrations of ferric oxide are generally not necessary to produce filtrates having strong color characteristics. For instance, in an otherwise non-absorbing material (e.g. clay, silica, alumina), as little as a few percent ferric iron content can produce a spectrum having strong absorption characteristics from the UV through most of the visible wavelengths, with little absorption in the near-IR. In such an instance, optimization of the emitters 24 and detectors 28 should take into account the spectral characteristics of both the particulate 30 and the non-turbid fluid within the filtrate 50. With pure water being the non-turbid fluid within the filtrate 50, a short operating wavelength will likely give a maximum sensitivity to solids, which is desirable for detecting low solids concentrations over a short optical path length. Conversely, if higher solids concentrations are to be measured and/or the optical path length is longer, a longer-wavelength in the red or near-IR would be more desirable, where ferric oxide is less strongly absorbing. In the case of copper-rich filtrates, the spectrum of the liquid fraction of the filtrate 50 would limit practical operation to wavelengths of about 550 nm and shorter. At these wavelengths, iron-rich solids would behave similar to copper concentrate and other very dark solids—essentially black.

Example 12

Yet another example of optimizing and tailoring turbidity sensing module components based on filtrate 50 and particulate 30 compositions might comprise adapting emitters 24 and detectors 28 to work well with iron-rich liquids and iron-rich solids simultaneously, each having similar spectral characteristics. In such cases, considering just the liquid fraction of the filtrate 50, the operating wavelength should be as long as possible, preferably in the near infrared (NIR), where the liquid is most transparent. However, sensitive detection of iron-rich solids during turbidity measurement generally dictates using shorter wavelengths, where the solid is more strongly absorbing. Clearly, in this case, tradeoffs will need to be carefully considered when determining the optimal operational wavelength ranges for the emitters 24 and detectors 28. Other factors should also be considered, including: the range of the solids concentration of interest, the optical path length, and the optimization of scattering measurements by off-angle 47a, 48b optical detectors 28b, 28c.

From the above examples, which have been shown for practical, exemplary, and non-limiting purposes only, it can be seen that measurement schemes vary from simple to complex, depending on how much accuracy and sensitivity is desired for a given turbidity measurement application. It is therefore anticipated that the any one or more of the implementation options discussed herein may be used singly or in concert.

Figures 14, 15:
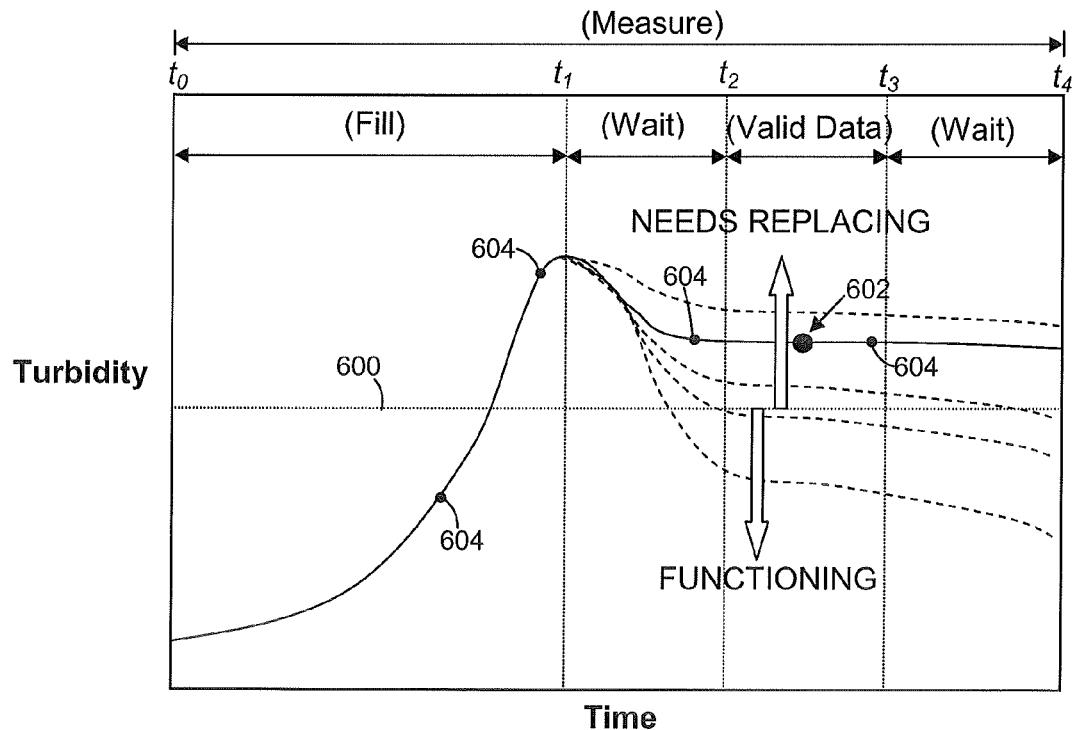
FIG. 14 is a table indicating the default values for a local or remote alarm according to some embodiments.
FIG. 15 is a graph schematically illustrating turbidity over time during an exemplary filtration cycle of a filter press.

Instantaneous turbidity 604 may be calculated at different times during a filtration cycle (FIG. 15). If, at any particular point in time or timeframe within a filtration cycle (e.g., between time $t_2$ and $t_3$), the average 602 of instantaneous turbidity 604 of the filtrate 50 is deemed to be greater than a predetermined threshold value 600, the control system 70 may issue a fault code (e.g., a binary "0" or "false" value), which triggers an alarm 80. The alarm 80 may indicate to an operator that the filter cloth associated with a particular filter plate assembly 1 needs servicing or replacement. After the alarm 80 is reset, the control system may issue a rectified code (e.g., a binary "1" or "true" value), which disables the alarm 80. In some embodiments, the alarm 80 may be reset by waving a magnetic reset wand 97 in close proximity to the turbidity sensing module 20, interface unit 60, or control system 70 which, in turn, resets a trip switch in a similar fashion to what is described in U.S. Pat. No. 4,837,552. In other embodiments, the alarm 80 may be reset with a keystroke from a remote operator control panel or by pressing a reset button on a portable control device.

In some embodiments, individual turbidity sensing modules 20, 220, 320, 420 on filter plate assemblies of a filter press may remain on a power-saving "standby" status during normal filter operation, wherein a main turbidity sensing module (not shown) may be located at the main filtrate discharge of a filter press. The main turbidity sensing module may serve to continually monitor the instantaneous turbidity 604 of all of the filtrate 50 exiting the filter press collectively, as a whole. If, at any point or timeframe within operation, the filtrate turbidity leaving the filter press (collectively, as a whole) exceeds a certain predetermined threshold 600, the control system 70 may instruct the individual turbidity sensing modules 20, 220, 320, 420 provided with each filter plate assembly 1 to be removed from standby status and activated at full power, in order to determine which of the filter plate assemblies 1 in the stack is causing the increased filtrate turbidity. Accordingly, turbidity sensing modules 20, 220, 320, 420 disclosed herein may be adapted to function in various capacities during different situations without limitation.

Figure 13:
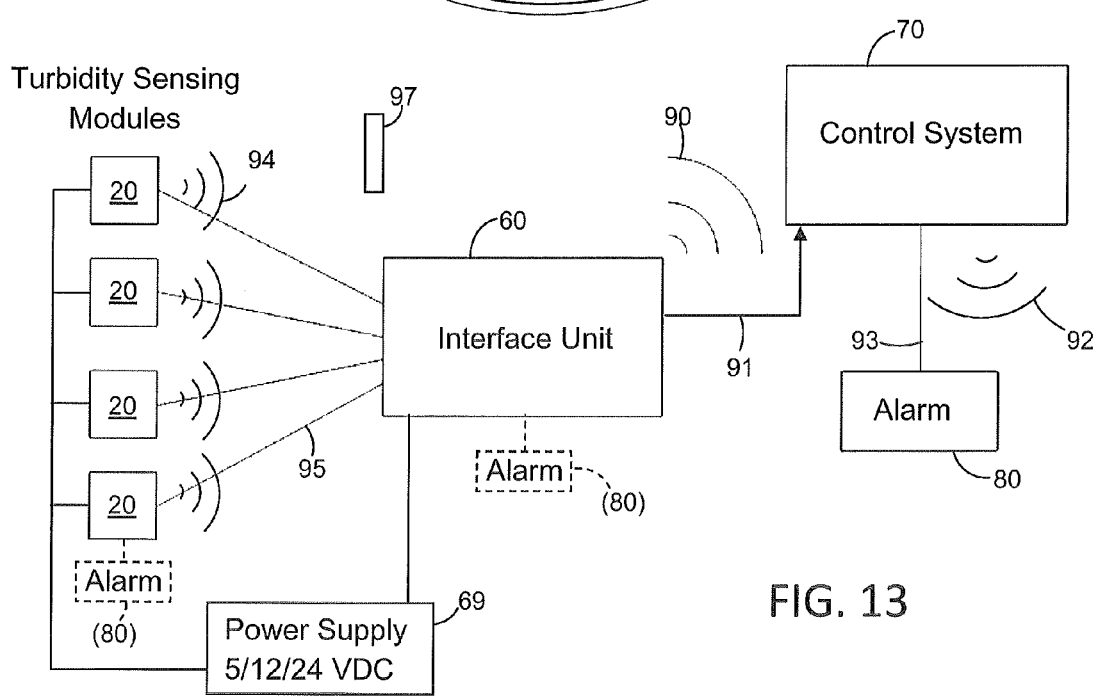
FIG. 13 is a schematic representation showing a turbidity sensing system according to some embodiments.

FIG. 13 is a schematic representation showing a turbidity sensing system according to some embodiments. One or more turbidity sensing modules 20 on the same or different filter plate assemblies 1 communicate with an interface unit 60 via wireless 94 or hard wired means 95. The interface unit 60 may be separate from or integral with the turbidity sensing modules 20, 220, 320, 420 themselves, a filter plate assembly 1, or a filter press as a whole. The interface unit 60 communicates with a control system 70 via wireless 90 or hard wired means 91. The control system may also be separate or integrally-provided with the turbidity sensing modules themselves, the filter plate assembly, or the filter press as a whole. An alarm 80 may be operably connected to the control system 70, interface unit 60, or turbidity sensing modules 20 via wireless 92 or hard wired means 93. One or more power supplies 69, for instance, a direct current power supply such as a battery may be provided to one or more of the turbidity sensing modules 20, interface unit 60, control system 70, or alarm 80. In some embodiments, a magnetic reset wand 97 may be used to reset the alarm 80 which moves (without physical contact) a magnetic trip switch when the reset wand 97 comes within proximity of the alarm 80. It will be understood to those having an ordinary skill in the art that the reset wand 97 may alternatively utilize RFID or other remote or touchless proximity technologies. Moreover, reset of the alarm 80 may be done physically by pressing a reset button operably connected to the alarm and control system 70.

For any one of the aforementioned embodiments, a power source 69, such as a 12 VDC battery may be provided within the turbidity sensing module 20, 220, 320, 420, external modules 2, or integral modules 3 described. Moreover, a control system 70 may be provided to any one or more of the turbidity sensing modules 20, 220, 320, 420, external modules 2, integral modules 3, or filter plate assemblies 1 shown. The control system 70 may comprise, for instance, a programmable logic controller (PLC) or programmable automation controller (PAC) with one or more prewired serial ports, modules, cables 6, serial bus interfaces, or other wireless communication technologies which are well-known in the art (e.g., 1 Mbits/s Bluetooth; 802.11 Wi-Fi; 20, 40, or 250 Kbits/s ZigBee®; 100-500 Mbits/s Ultra Wide Band; 62.5 Kbits/s Wireless USB; 20-40 Kbits/s, 115 Kbits/s, or 4 & 16 Mbits/s IR Wireless). Parallel bus interfaces and wireless communication technologies may be incorporated to allow modules 2 between filter plate assemblies 1 to communicate on a single bus or platform. Supervisory control and data acquisition (SCADA) platforms may be advantageously utilized in order to provide CPU functionality to the turbidity sensing system whilst maintaining the simplicity and reliability of the PLC.

An alarm 80 may also be provided to any of the deep turbidity sensing modules 420 or modules 2, 3 in order to signal a failing filter cloth, verify a functioning filter cloth, determine an error in the software, or detect broken hardware in the turbidity sensing system. The alarm might comprise, for instance, a light source such as one or more bright LEDs. Multiple LEDs having different colors may be used to indicate various degrees of alarm or different statuses.

For example, a green colored LED may be energized in order to signal a properly operating filter plate assembly 1 and/or a properly operating turbidity sensing module 20. An orange colored LED, when on, may indicate that local turbidity is rising and that a filter cloth change for a particular filter plate assembly 1 is imminent in the near future. A red colored LED, when on, may indicate a current failure of some sort, such as a severely damaged filter cloth. Multi-color LEDs may also be utilized in the alarms, as well as single color LEDs. In some embodiments, the LEDs may be pre-programmed to blink at different frequencies or glow at different brightnesses in order to convey different meanings. For example, a quickly-pulsing single LED may signal that filter cloth maintenance is immediately necessary for a given filter plate assembly 1, whereas a slow pulsing of the single LED alarm 80 may signal that filter cloth maintenance on a particular filter plate assembly 1 can be postponed for a given time or indefinitely. Alternatively, a non-pulsing, solid glow may serve as a check indicator that an internal battery, external wire, or other power source 69 is still fully operational. In some instances, LEDs may serve to indicate that turbidity sensing modules 20, 420 or retrofit units 4, 5 are faulty (e.g., by blinking in various patterns or Morse code).

Alarms 80 may be alternatively provided as sound buzzers having various tones, pitches, frequencies, or melodies to indicate different information. Electronic signals, for example, in the form of one or more constant or varying voltages may be relayed to a control system 70. In some embodiments, the electronic signals could form one or more of a plurality of predetermined character messages on a large electronic display board. In some embodiments, the electronic signal may affect a control parameter of the filter press (e.g., engage a kill switch, adjust cycle time, etc). Such alternative alarms may be used alone or in concert with any one or more of the visual alarms described above.

In order to ensure that the gaps 31, 431 of turbidity sensing modules 20, 220, 320, 420 disclosed herein are correctly oriented to be in proper alignment with the drain channels 18a-d, a single-orientation key feature may be employed on the mounting plate 29, 429. Such a key feature may be a protrusion which may be accepted in a recess within a filter plate assembly 1 in only a single spatial orientation. Alternatively, such a key feature may be provided by mounting holes 29b, 429b arranged in a unique pattern which will only match up with other portions of the filter plate assembly 1 in a single orientation. By controlling or varying the thicknesses of mounting plates 29, 429 or overall lengths of housings 22, 422, the depth of insertion of the turbidity sensing modules 20, 220, 320, 420 into turbidity measurement chambers 19 may be controlled, further optimizing placement of the optical emitters 24 and detectors 28 within filtrate streams flowing through the drain channels 18a-d. One or more special shims may be used between the mounting plates 29, 429 and the filter plate assembly 1 in order to change the measurement location within the drain channels 18a-d.

A contractor or other entity may provide a turbidity sensing system or install a turbidity sensing apparatus according to a process in whole, or in part, as shown and described. For instance, the contractor may receive a bid request for a project related to designing turbidity sensing system, or the contractor may offer to design or provide such an apparatus or system for a client. The contractor may then provide, for example, any one or more of the devices or features thereof shown and/or described in the embodiments discussed above. The contractor may provide such devices by selling those devices or by offering to sell those devices. The contractor may provide various embodiments that are sized, shaped, and/or otherwise configured to meet the design criteria of a particular client or customer. The contractor may subcontract the fabrication, delivery, sale, or installation of a component or whole of the devices disclosed, or of other devices used to provide said devices. The contractor may also survey a site and design or designate one or more storage areas for stacking the material used to manufacture the devices. The contractor may also maintain, modify, replace, or upgrade the provided devices. The contractor may provide such maintenance or modifications by subcontracting such services or by directly providing those services or components needed for said maintenance or modifications, and in some cases, the contractor may modify an existing filter press, filter plate assembly, or other filtration unit with a "retrofit kit" to arrive at a modified filter press or component thereof which comprises one or more method steps, devices, or features of the turbidity sensing technologies discussed herein.

Although the invention has been described in terms of particular embodiments and applications, one of ordinary skill in the art, in light of this teaching, can generate additional embodiments and modifications without departing from the spirit of or exceeding the scope of the claimed invention. For example, it is envisaged that any one or more of the turbidity sensing configurations shown in FIGS. 3-8 may be used alone or in combination with one another in any conceivable pattern, number, or arrangement. Moreover, it is envisaged that one or more features, concepts, or methods of the invention may be practiced with various other types of filtration equipment including, but not limited to candle filters, horizontal belt filters, vertical pressure leaf filters, horizontal stacking plate filter presses, Pneumapress® automatic pressure filters (which are currently offered by Applicant), rotary vacuum drum filters, and vacuum disk filters. For example, in a candle filter, one or more of the turbidity sensing modules disclosed herein may be used to determine clarity of filtrate during an alumina manufacturing process. In another non-limiting example, one or more of the turbidity sensing modules disclosed herein may be positioned on or within bottom portions of a vacuum pan tray of a horizontal belt filter to monitor the turbidity of filtrate at particular washing stations and monitor the condition of the filter cloth. Accordingly, it is to be understood that the drawings and descriptions herein are proffered by way of example to facilitate comprehension of the invention and should not be construed to limit the scope thereof.

REFERENCE NUMERAL LIST

1 Filter plate assembly
2 External module
3 Integral module
3a Casing
4 First retrofit unit
4a Housing body
4b Transverse drain channel
4c Lower vertical drain channel
4d Upper vertical drain channel
4e Connector
4f Plug
4g Filtrate discharge tube
5 Second retrofit unit
6 Cable
7 Filtrate port (upper)
8a-d Filtrate drain openings (upper, side, lower, inboard)
9 Stay boss
10 Feed eye
11 Peripheral sealing surface
13 Filtrate port (lower)
14 Filter chamber
15 Filtrate discharge tube
18a-d Drain channel (upper, side, lower, inboard)
19 Turbidity measurement chamber
20 Turbidity sensing module (shallow)
21 O-ring
22 Housing
24 Optical emitter
24a-b Optical emitters 25 Potting material
27 Groove
28 Optical detector (e.g., phototransistor/photodiode)
28a-c Optical detectors (e.g., phototransistor/photodiode)
29 Mounting plate
29a Holding portion (e.g., recess)
29b Mounting hole
29c Threaded hole (removal jackscrew)
29d Gasket
30 Particulate
31 Gap
32 Electromagnetic radiation
41 First direction
42 Second direction
43 Third direction
44 Fourth direction
45 Fifth direction
46 Sixth direction
47a First angle
47b Second angle
48a Third angle
48b Fourth angle
50 Filtrate
60 Interface unit
69 Power source
70 Control system
80 Alarm (e.g., light, sound buzzer, electronic signal)
90, 92, 94 Wireless communication
91, 93, 95 Hard wired communication
97 Magnetic reset wand
220 Turbidity sensing module (shallow)
320 Turbidity sensing module (deep)
420 Turbidity sensing module (deep)
421 O-ring
422 Housing
423 Circuitry enclosure
423A Lateral openings
423B Central opening
424 Optical emitter
425 Potting material
426 Printed circuit board
426B Wire
427 Groove
428 Optical detectors
429 Mounting plate
429a Holding portion (e.g., recess)
429b Mounting hole
429c Threaded hole (jackscrew)
429d Gasket
430 Fastener (e.g., screw)
431 Gap
600 Upper threshold of functioning cloth
602 Average instantaneous turbidity between $t_2$ and $t_3$
604 Instantaneous turbidity

We claim:

1. A horizontal filter press comprising:
a frame;
a plurality of horizontally-stackable, vertically-disposed, and horizontally movable filter plate assemblies [1] supported by the frame;
the filter plate assemblies [1] forming a plate stack which extends horizontally, the filter plate assemblies [1] each being configured to support a filter cloth;
a first turbidity sensing module [20, 220, 320, 420] coupled to a first filter plate assembly [1] within the plurality of stackable filter plate assemblies [1]; and
a second turbidity sensing module [20, 220, 320, 420] coupled to a second filter plate assembly [1] within the plurality of stackable filter plate assemblies [1];
wherein the first filter plate assembly [1] and the second filter plate assembly [1] are configured to horizontally come into close proximity with each other to form and hold a filter cake therebetween; the first filter plate assembly [1] and the second filter plate assembly [1] being further configured to move horizontally away from each other, in order to release and vertically discharge said filter cake;
wherein the first turbidity sensing module [20, 220, 320, 420] is positioned between a filtrate drain opening [8a-d] of the first filter plate assembly [1] communicating with a filter chamber [14] of the first filter plate assembly [1], and a filtrate port [7, 13] or filtrate discharge tube [4g, 15] of the first filter plate assembly [1]; and
wherein the second turbidity sensing module [20, 220, 320, 420] is positioned between a filtrate drain opening [8a-d] of the second filter plate assembly [1] communicating with a filter chamber [14] of the second filter plate assembly [1], and a filtrate port [7, 13] or filtrate discharge tube [4g, 15] of the second filter plate assembly [1], in order to determine a level of turbidity of filtrate [50] exiting said first filter plate assembly [1] independently of a level of turbidity of filtrate [50] exiting the second filter plate assembly [1].

2. The filter press according to claim 1, wherein the first or second filter plate assembly [1] comprises a plurality of turbidity sensing modules [20, 220, 320, 420].

3. The filter press according to claim 1, wherein more than two filter plate assemblies [1] within the plurality of stackable filter plate assemblies [1] comprise at least one turbidity sensing module [20, 220, 320, 420].

4. The filter press according to claim 1, wherein the first or second turbidity sensing module [20, 220, 320, 420] comprises at least one optical emitter [24, 424] and at least one optical detector [28, 428].

5. The filter press according to claim 4, wherein the number of optical detectors [28, 428] exceeds the number of optical emitters [24, 424].

6. The filter press according to claim 5, wherein the optical detectors [28, 428] are provided at different angles [27a, 27b, 28a, 28b] with respect to the at least one optical emitter [24, 424].

7. The filter press according to claim 4, wherein each optical detector [28, 428] measures and determines an amount of electromagnetic radiation [32] received by each optical emitter [24, 424], and wherein the first or second turbidity sensing module [20] provides signal information regarding the same, to an interface unit [60].

8. The filter press according to claim 7, wherein the interface unit [60] communicates with a control system [70] and/or an alarm [80] via hard wired [91, 93, 95] or wireless [90, 92, 94] communication means.

9. The filter press according to claim 1, wherein the first turbidity sensing module [20, 220, 320, 420] is inserted into a turbidity measurement chamber [19] provided to the first filter plate assembly [1], the turbidity measurement chamber [19] intersecting the drain channel [4b, 18a-d].

10. The filter press according to claim 1, wherein the first or second turbidity sensing module [20, 220, 320, 420] comprises a housing [22, 422] defining a circuitry enclosure [423], a circuit board [426], at least one optical emitter [24, 424], at least one optical detector [28, 428].

11. A replacement filter plate assembly [1] for a horizontal filter press, the horizontal filter press having a frame, a plurality of horizontally-stackable, vertically-disposed, and horizontally movable filter plate assemblies [1] supported by the frame; the filter plate assemblies [1] forming a plate stack which extends horizontally, the filter plate assemblies [1] each being configured to support a filter cloth; a first turbidity sensing module [20, 220, 320, 420] coupled to a first filter plate assembly [1] within the plurality of stackable filter plate assemblies [1]; and a second turbidity sensing module [20, 220, 320, 420] coupled to a second filter plate assembly [1] within the plurality of stackable filter plate assemblies [1]; wherein the first filter plate assembly [1] and the second filter plate assembly [1] are configured to horizontally come into close proximity with each other, in order to form a filter cake and hold the filter cake therebetween; the first filter plate assembly [1] and the second filter plate assembly [1] being further configured to move horizontally away from each other, in order to release and vertically discharge said filter cake;

wherein the first turbidity sensing module [20, 220, 320, 420] is positioned between a filtrate drain opening [8a-d] of the first filter plate assembly [1] communicating with a filter chamber [14] of the first filter plate assembly [1], and a filtrate port [7, 13] or filtrate discharge tube [4g, 15] of said first filter plate assembly [1]; and wherein the second turbidity sensing module [20, 220, 320, 420] is positioned between a filtrate drain opening [8a-d] of the second filter plate assembly [1] communicating with a filter chamber [14] of the second filter plate assembly [1], and a filtrate port [7, 13] or filtrate discharge tube [4g, 15] of said second filter plate assembly [1], in order to determine a first level of turbidity of filtrate [50] exiting said first filter plate assembly [1] independently of a level of turbidity of filtrate [50] exiting said second filter plate assembly [1], the replacement filter plate assembly [1] comprising:

a turbidity sensing module [20, 220, 320, 420] coupled to the replacement filter plate assembly [1]; wherein the turbidity sensing module [20, 220, 320, 420] is positioned between a filtrate drain opening [8a-d] of the replacement filter plate assembly [1] communicating with a filter chamber [14] of the replacement filter plate assembly [1], and a filtrate port [7, 13] or filtrate discharge tube [4g, 15] of the replacement filter plate assembly [1], in order to determine a level of turbidity of filtrate [50] exiting said replacement filter plate assembly [1] independently of a level of turbidity of filtrate [50] exiting the first filter plate assembly [1] or the second filter plate assembly [1].

12. The replacement filter plate assembly [1] according to claim 11, further comprising a plurality of turbidity sensing modules [20, 220, 320, 420].

13. The replacement filter plate assembly [1] according to claim 11, wherein the turbidity sensing module [20, 220, 320, 420] comprises at least one optical emitter [24, 424] and at least one optical detector [28, 428].

14. The replacement filter plate assembly [1] according to claim 13, wherein the turbidity sensing module [20, 220, 320, 420] comprises a number of optical detectors [28, 428] which exceeds the number of optical emitters [24, 424].

15. The replacement filter plate assembly [1] according to claim 14, wherein the optical detectors [28, 428] are provided at different angles [27a, 27b, 28a, 28b] with respect to the at least one optical emitter [24, 424].

16. The replacement filter plate assembly [1] according to claim 13, wherein each optical detector [28, 428] measures and determines an amount of electromagnetic radiation [32] received by each optical emitter [24, 424], and wherein each optical detector [28, 428] provides signal information regarding the same, to an interface unit [60].

17. The replacement filter plate assembly [1] according to claim 11, wherein the turbidity sensing module [20, 220, 320, 420] is inserted into a turbidity measurement chamber [19] which is provided to the replacement filter plate assembly [1], the turbidity measurement chamber [19] intersecting a drain channel [4b, 18a-d].

18. The replacement filter plate assembly [1] according claim 11, wherein the turbidity sensing module [20, 220, 320, 420] comprises a housing [22, 422] having a circuitry enclosure containing a circuit board [426], at least one optical emitter [24, 424], at least one optical detector [28, 428].

19. The replacement filter plate assembly [1] according to claim 18, wherein a gap [31, 431] is provided between the at least one optical emitter [24, 424] and the at least one optical detector [28, 428], and a portion of said gap [31, 431] is lined with a protective wear plate to reduce abrasion from the filtrate [50].

20. A retrofit unit [4, 5] for monitoring turbidity of a filtrate produced by a first filter plate assembly [1] within a plurality of horizontally stackable, vertically-disposed, and horizontally movable filter plate assemblies [1] of a horizontal filter press, or, for monitoring turbidity of a filtrate produced by a second filter plate assembly [1] within the plurality of horizontally stackable filter plate assemblies [1] of the horizontal filter press, and being configured for attachment to the first filter plate assembly [1] or to the second filter plate assembly [1]; the horizontal filter press having a frame supporting said plurality of horizontally stackable filter plate assemblies [1]; the plurality of horizontally stackable, vertically-disposed, and horizontally movable filter plate assemblies [1] forming a plate stack which extends horizontally; the filter plate assemblies [1] each being configured to support a filter cloth; the first filter plate assembly [1] having a filtrate drain opening [8a-d] communicating with a filter chamber [14], and a filtrate port [7, 13] or filtrate discharge tube [4g, 15]; the second filter plate assembly [1] having a filtrate drain opening [8a-d] communicating with a filter chamber [14], and a filtrate port [7, 13] or filtrate discharge tube [4g, 15]; wherein the first filter plate assembly [1] and the second filter plate assembly [1] are configured to horizontally come into close proximity with each other, in order to form a filter cake and hold the filter cake therebetween; the first filter plate assembly [1] and the second filter plate assembly [1] being further configured to move horizontally away from each other, in order to release and vertically discharge said filter cake; the retrofit unit [4, 5] comprising:

at least one turbidity sensing module [20, 220, 320, 420] which is configured to be positioned between a filtrate drain opening [8a-d] of the first filter plate assembly [1] communicating with a filter chamber [14] of the first filter plate assembly [1], and a filtrate port [7, 13] or filtrate discharge tube [4g, 15] of the first filter plate assembly [1]; the at least one turbidity sensing module [20, 220, 320, 420] also being configured to be positioned between a filtrate drain opening [8a-d] of the second filter plate assembly [1] communicating with a filter chamber [14] of the second filter plate assembly [1], and a filtrate port [7, 13] or filtrate discharge tube [4g, 15] of the second filter plate assembly [1], in order to determine a level of turbidity of filtrate [50] exiting said first filter plate assembly [1] independently of a level of turbidity of filtrate [50] exiting said second filter plate assembly [1].

* * * * *